US012544529B2

(12) United States Patent
Walls et al.

(10) Patent No.: US 12,544,529 B2
(45) Date of Patent: Feb. 10, 2026

(54) APPARATUS FOR DELIVERING A GAS STREAM

(71) Applicant: Fisher & Paykel Healthcare Limited, Auckland (NZ)

(72) Inventors: Bruce Michael Walls, Auckland (NZ); Peter Lawrence Grylls, Auckland (NZ); Douglas Richard Wright, Auckland (NZ); Christopher Earl Nightingale, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1063 days.

(21) Appl. No.: 17/596,565

(22) PCT Filed: Jun. 12, 2020

(86) PCT No.: PCT/NZ2020/050061

§ 371 (c)(1),
(2) Date: Dec. 13, 2021

(87) PCT Pub. No.: WO2020/251376

PCT Pub. Date: Dec. 17, 2020

(65) Prior Publication Data

US 2022/0379068 A1 Dec. 1, 2022

Related U.S. Application Data

(60) Provisional application No. 62/935,867, filed on Nov. 15, 2019, provisional application No. 62/861,515, filed on Jun. 14, 2019.

(51) Int. Cl.
*A61M 16/16* (2006.01)
*A61M 16/00* (2006.01)
(Continued)

(52) U.S. Cl.
CPC ........ *A61M 16/16* (2013.01); *A61M 16/0066* (2013.01); *A61M 16/109* (2014.02);
(Continued)

(58) Field of Classification Search
CPC .............. A61M 16/16; A61M 16/0066; A61M 16/109; A61M 16/202; A61M 16/20;
(Continued)

(56) References Cited

U.S. PATENT DOCUMENTS 5,228,107 A 7/1993 Marino
7,478,635 B2 1/2009 Wixey et al.
(Continued)

FOREIGN PATENT DOCUMENTS

WO WO 2007/038152 A2 4/2007
WO WO 2014/138804 A1 9/2014
WO WO 2016/207838 A1 12/2016

OTHER PUBLICATIONS

International Search Report for International Application No. PCT/NZ2020/050061 dated Oct. 2, 2020.
(Continued)

*Primary Examiner* — Tu A Vo
*Assistant Examiner* — Kelsey E Baller
(74) *Attorney, Agent, or Firm* — VIA LLP

(57) ABSTRACT

The present invention relates to an apparatus for providing respiratory assistance to a user via a user conduit. The apparatus being operable in a humidifying mode and a non-humidifying mode, and includes a humidification chamber for containing an amount of water that can be located in an operating position in the humidifying mode and, optionally separate from the apparatus in the non-humidifying mode. The apparatus may also have an auxiliary flow path that can be activated in the non-humidifying mode and a
(Continued)

powered device that heats water in the humidification chamber when the apparatus is in the humidifying mode.

13 Claims, 11 Drawing Sheets

(51) Int. Cl.
*A61M 16/10* (2006.01)
*A61M 16/20* (2006.01)

(52) U.S. Cl.
CPC ... *A61M 16/202* (2014.02); *A61M 2205/3633* (2013.01); *A61M 2205/368* (2013.01); *A61M 2205/505* (2013.01)

(58) Field of Classification Search
CPC ............ A61M 16/0816; A61M 16/107; A61M 16/1085; A61M 16/1095; A61M 2205/3633; A61M 2205/368; A61M 2205/505; A61M 2202/0208; A61M 2205/21; A61M 2205/3653; A61M 2205/42; A61M 2205/6045; A61M 2205/8206; A61M 2205/8262; A61M 2205/586; A61M 2209/086
See application file for complete search history.

(56) References Cited

U.S. PATENT DOCUMENTS

| | | | | |
|---|---|---|---|---|
| 7,909,032 | B2 | 3/2011 | Feldhahn et al. | |
| 8,020,551 | B2 | 9/2011 | Virr et al. | |
| 2008/0245365 | A1* | 10/2008 | Genger | A61M 16/16 392/394 |
| 2014/0264975 | A1* | 9/2014 | Bath | A61M 16/16 261/141 |
| 2015/0115483 | A1* | 4/2015 | Miller | A61M 16/024 261/142 |
| 2015/0258300 | A1 | 9/2015 | Lin et al. | |
| 2016/0228671 | A1* | 8/2016 | Jackson | A61M 16/109 |
| 2017/0361053 | A1* | 12/2017 | Dimatteo | A61M 16/024 |

OTHER PUBLICATIONS

Supplementary European Search Report for European Application No. EP 20 82 1910 dated May 30, 2023.

* cited by examiner

*Figure 14*

| Humidification mode | Non-humidification mode |
|---|---|
| • Providing a housing having a gas stream outlet port and a gas stream inlet port.<br>• Operating a blower to generate a gas stream.<br>• Locating a humidification chamber in an operating position in which an inlet of the chamber communicates with the outlet port of the housing, and in which an outlet of the chamber communicates with the inlet port of the housing.<br>• Moving an auxiliary flow path into an inactive position in which the salary flow path is remote from the inlet port and the outlet port.<br>• Conveying the gas stream through the humidification chamber to humidify the gas stream.<br>• Conveying the humidified gas stream to a user. | • Providing a housing having a gas stream outlet port and a gas stream inlet port.<br>• Operating a blower to generate a gas stream.<br>• Removing the humidification chamber from the operating position.<br>• Moving the auxiliary flow path into an active position in which the auxiliary flow path communicates with the inlet port and the outlet port and conveys the gas stream therebetween.<br>• Conveying the non-humidified gas stream to a user. |

APPARATUS FOR DELIVERING A GAS STREAM

RELATED APPLICATIONS

The present application is a U.S. National Phase Application of International Application No. PCT/NZ2020/050061, filed on Jun. 12, 2020, which claims priority to U.S. provisional patent application No. 62/861,515 filed on 14 Jun. 2019 and U.S. provisional patent application No. 62/935,867 filed on 15 Nov. 2019. The specifications of application nos. PCT/NZ2020/050061, 62/86151, and 62/935867 are hereby incorporated into this specification by express reference.

FIELD OF THE INVENTION

The present invention relates to an apparatus for delivering a gas stream to a user and a method of operating the apparatus. The gas stream can be used to provide respiratory assistance and can, for example, be used in Positive Airway Pressure (PAP) therapy for the treatment of disorders such as sleep apnea.

BACKGROUND

The terms “respiratory assistance,”, “apparatus for providing respiratory assistance”, or variations thereof, as used in this specification, embraces respirator/therapies such as, but not limited to, Positive Airway Pressure (PAP) therapies, including but not limited to CPAP therapy and Bi-level therapy, Non-Invasive Ventilation (NIV), and Nasal High Flow therapy (NHF) which can be used for the treatment of diseases such as Obstructive Sleep Apnea (OSA), snoring, or Chronic Obstructive Pulmonary Disease (COPD).

There are a number of different respiratory therapy apparatuses presently on the market. Many of these apparatuses humidify the gas stream being supplied to the user to increase user comfort. A subset of these can be switched between a humidifying mode and a non-humidifying mode, for example via the addition of a separate, standalone humidifier placed in-line between the respiratory therapy apparatus and a breathing conduit. The conduit is required in both modes to convey a gas stream from the apparatus to the user. To accommodate the switch, some respiratory therapy apparatuses require the user to manually adjust the apparatus. For example, the user may be required to manually disconnect the conduit from one outlet and reconnect it to another outlet. Such a manual adjustment can be problematic for users having poor hand dexterity or users who do not find these steps intuitive.

There is therefore a need for another apparatus that is more intuitive and less physically demanding to switch between different modes of use.

SUMMARY OF THE INVENTION

An embodiment of the present invention relates to an apparatus for providing respiratory assistance to a user via a user conduit, the apparatus being operable in a humidifying mode and a non-humidifying mode, wherein the apparatus includes:

a blower for generating a gas stream;

an adjustable flow path for the gas stream to which the user conduit can be connected;

a housing having at least part of the adjustable flow path that extends from the blower to a housing outlet port;

a humidification chamber having a chamber inlet and the humidification chamber being movable and can be located in:

i) an operating position in which the chamber inlet communicates with the housing outlet port to convey the gas stream through the humidification chamber, the humidification chamber forming part of the adjustable flow path which operates the apparatus in the humidifying mode, and ii) a non-operating position in which the humidification chamber is separate from the housing, and does not form part of the adjustable flow path which operates the apparatus in the non-humidifying mode.

The adjustable flow path may include a conduit port that includes either a chamber conduit port and/or a housing conduit port to which the user conduit can be connected.

For example, the chamber conduit port may be located on the humidification chamber for the gas stream to exit directly from the humidification chamber. The user conduit may be connected to the chamber conduit port when the apparatus is in the humidifying mode.

In another example, the housing conduit port may be located on the housing. The user conduit may be connected to the housing conduit port when the apparatus is in the humidifying mode or the non-humidifying mode. One of the advantages in this arrangement is that the gas stream conduit does not require disconnection and reconnection to different ports when changing between the humidifying and the non-humidifying modes.

The adjustable flow path may have a return configuration when the apparatus is in the humidifying mode, in which the flow path extends from the housing to the humidification chamber, and returns to the housing.

The housing may have a housing inlet port and the humidification chamber may have a chamber outlet, and when the humidification chamber is in the operating position the adjustable flow path may have a return configuration that extends from the housing outlet port to the humidification chamber via the chamber inlet, and returns to the housing inlet port via the chamber outlet.

The adjustable flow path may include a fixed section extending from the housing inlet port to the housing conduit port.

The adjustable flow path may include a removable (unfixed) section extending from the housing inlet port to the housing conduit port.

The removable section may be detachably connected to the housing. The removable section may be suitable for conveying the gas stream when humidified and may require disinfecting or cleaning in accordance with a hygiene regime.

The removable section may include the housing inlet port, the conduit outlet port and a passageway extending therebetween.

The adjustable flow path may have a non-return configuration when the apparatus is in the humidifying mode, in which the flow path exits the humidification chamber without returning to the housing.

The housing outlet port may be connectable to the user conduit when the apparatus is in the non-humidifying mode and the humidification chamber is in the non-operative position. That is to say, the housing outlet port communicates with the chamber inlet when the humidification chamber is in the operating position, and the housing outlet is connectable to the user conduit when the humidification chamber is in the non-operating position.

The user conduit may be connectable to the housing outlet port irrespective of whether the adjustable flow path has a return configuration in the humidifying mode or a non-return configuration in the humidifying mode.

The housing may have a housing inlet port, and the apparatus may also include an auxiliary flow path section that that can be located in an active position when the apparatus is in the non-humidifying mode, and in which the auxiliary flow path section communicates with the housing outlet port and the housing inlet port to convey the gas stream therebetween.

The auxiliary flow path may be pivotally connected to the housing and can pivot between the active and the inactive positions.

the auxiliary flow path may be in the active position when the apparatus is in the non-humidifying mode, such that the path inlet and the path outlet are connected with the housing outlet port and housing inlet port respectively. In other words, to switch to the non-humidifying mode, the auxiliary flow path is moved to connect the path inlet and the path outlet to the housing outlet and inlet ports respectively.

The auxiliary flow path may move into the inactive position when the apparatus is in the humidifying mode, such that the path inlet and the path outlet are disconnected from the housing outlet port and the housing inlet port respectively.

The user conduit may be connected to the housing conduit port when the auxiliary flow path section is in the active position.

The auxiliary flow path section may be movably connected to the housing so as to move relative to the housing.

When the adjustable flow path does not have an auxiliary flow path section, the user conduit may be connected to the housing outlet port when the apparatus is in the non-humidifying mode.

In this situation, the adjustable flow path will change configuration by the humidification chamber being located in the operative position, which may require the user conduit being disconnected from the housing outlet port to allow connection of the chamber inlet to the housing outlet port.

It is also possible that the user conduit may be connected to the housing conduit port when the apparatus is in the non-humidifying mode.

The auxiliary flow path section may also be movable into an inactive position in which the auxiliary section is remote from the housing outlet port and the housing inlet port so the humidification chamber can be located in the operating position when the apparatus is in the humidifying mode.

Although it is possible that the apparatus can operate with the humidification chamber and the auxiliary section of flow path simultaneously communicating with the housing outlet port and the housing inlet port, it is preferred that the humidification chamber and the auxiliary flow path section are in flow communication with the housing inlet port and the housing outlet port alternatively.

In one embodiment, the apparatus may be operable in only one of the humidifying mode or the non-humidifying mode at one time. Positioning the auxiliary flow path remotely from the housing inlet port and the housing outlet port allows a user to place the humidification chamber in the operating position. That is to say, the chamber inlet and chamber outlet can be connected to the housing outlet port and the housing inlet port respectively.

One of the benefits provided by an embodiment is that a user can operate the apparatus in a humidifying mode whilst the user is at home or at their normal place of sleep, and when the user is travelling or away from their normal place of sleeping, the apparatus may be used in a non-humidifying mode, so that the user does not have to carry and transport the humidification chamber.

It is also possible that the apparatus could be operated in the non-humifying mode without the humification chamber being separate from the housing. For example, with the humidification chamber being empty of water. But ideally, the humidification chamber is separate from the housing so that the humidification chamber is in the non-operating position.

When the humidification chamber is in the non-operating position, the chamber inlet is displaced from the housing outlet port and the chamber outlet is displaced from the housing inlet port, and the auxiliary section of the flow path is able to be moved into the active position. In the other words, the chamber is displaced from the housing to accommodate the auxiliary section flow path moving into the active position.

When the humidification chamber is in the non-operating position, the humidification chamber is free to move relative to the housing or is detached from the housing. The humidification chamber may be manually removed from the apparatus by a user.

The humidification chamber may be separate from the housing when the apparatus is in the non-humidifying mode.

The humidification chamber may be attached to the housing when switching from the non-humidifying mode to the humidifying mode.

The humidification chamber may be loaded into the housing when the apparatus is in the humidifying mode. In this situation, the auxiliary flow path is in the inactive position.

The chamber inlet and the chamber outlet can communicate with the housing outlet port and the housing inlet port respectively in the humidifying mode.

The auxiliary flow path may be operable to communicate with the housing outlet and the housing inlet when the humidification chamber is separate from the housing. The humidification chamber may be separate from the housing and disconnected from the apparatus when in the non-humidification mode.

The humidification chamber may have an operating position in the humidifying mode in which the chamber inlet and the chamber outlet communicate with the housing outlet port and the housing inlet port respectively.

More particularly, the chamber inlet and the chamber outlet have defined fixed positions in a body of the humidification chamber, and the humidification chamber is able to be manually installed (by a user) relative to the housing so that the chamber inlet and the chamber outlet align with the housing outlet port and the housing inlet port respectively, thereby locating the humidification chamber in the operating position in the humification mode.

The humidification chamber may also have a non-operating position in which the humidification chamber is free to move relative to the housing or is detached from the housing. The humidification chamber may be manually removed from the apparatus by a user.

The housing may include a main body and a platform that is moveable relative to the main body.

The blower may be housed in the main body.

The housing inlet port and the housing outlet port may be located on the main body.

The auxiliary flow path may have a path inlet that can communicate with the housing outlet port and a path outlet that can communicate with the housing inlet port.

The path inlet and the path outlet of the auxiliary flow path can be connected to the housing outlet port and the housing inlet port respectively when the humidification chamber is separate from the housing.

The auxiliary flow path section may be pivotally connected to the housing and can pivot between the active and the inactive positions.

The auxiliary flow path section may move in a linear motion, such as on a sliding mechanism that moves inwardly and outwardly from the housing, between the active and the inactive positions. For instance, the auxiliary flow path may be mounted on a draw mechanism.

It is also possible that the auxiliary flow path section may be pivotally connected to a sliding mechanism in which case the movement of the auxiliary flow path will be a combination of different kinetics.

The auxiliary flow path section may be on the platform on which the path inlet and the path outlet are supported, and the platform is moveable relative to the housing.

At least part of the auxiliary flow path may be defined by the platform.

When the auxiliary flow path is in the active position, the platform has moved toward the housing such that the auxiliary flow path communicates with the housing inlet port and the housing outlet port.

In an alternative embodiment, the adjustable flow path may include a valve that can be switched to direct the gas stream from the blower to either one of: i) the housing outlet port; or ii) a conduit port on the housing.

Throughout this specification the term "valve" embraces a valve as a singular item and as multiple items, and therefore covers a plurality of valves. The valve may control the flow of the gas stream, for instance, turn the flow ON/OFF and/or direct the flow of the gas stream along two or more alternative paths as described, for instance, in the paragraph immediately above.

The valve may be operable to direct the gas stream from the blower to the housing outlet port when the apparatus in the humidifying mode.

The valve may be operable to direct the gas stream from the blower to the housing outlet port when the apparatus is in the humidifying mode or the non-humidifying mode.

The switchable valve may be operable to direct the gas stream from the blower to the conduit port of the housing when the apparatus is in the non-humidifying mode.

The valve may be switched by the user.

The apparatus may include an actuator for switching the valve, for example, when the platform is moved from the opened orientation to the closed orientation.

The actuator for switching the valve may be a mechanical actuator or an electrical actuator including a solenoid for operating the valve.

The humidification chamber may be separate from the housing when the apparatus is in the non-humidifying mode to allow the platform to be moved toward the housing to locate the auxiliary flow path section in the active position.

In the inactive position the platform has moved relative to the housing so that the auxiliary flow path is spaced from the housing outlet port and the housing inlet port. In other words, the inlet port and the outlet port are vacated which allows a user to locate the humidification chamber in the operating position.

When the auxiliary flow path section is in the inactive position, the humidification chamber can be loaded onto the housing so that the chamber inlet communicates with the housing outlet port. That is to say, the adjustable flow path may be in the return configuration.

The platform and the humidification chamber may be engaged when the auxiliary flow path is in the inactive position.

When the auxiliary flow path section is in the inactive position, the humidification chamber can be loaded onto the housing so that the chamber inlet and the chamber outlet communicate with the housing outlet port and the housing inlet port respectively.

The humidification chamber may engage the housing when the humidification chamber is in the operating position.

One of the benefits of the engagement between the humidification chamber and either one or both of the platform and the housing is that the engagement can help secure and stabilise the humidification chamber in the operating position when the apparatus is in the humidifying mode.

The platform may be pivotally connected relative to the housing. For instance, a first section of the platform has a pivot connection for pivotally connecting to the housing and the path inlet and the path outlet may be arranged at a second section of the platform.

In one example, the first section may be at or toward an end of the platform and the second section may be at or toward an opposite end of platform.

In another example, the first and second sections may be adjacent to each other.

The platform may have a rigid body.

The platform may be pivoted between opened and closed orientations.

The platform can be pivoted into a closed orientation in which the act of closing the platform moves the auxiliary flow path section to the active position. In other words, when the platform is pivoted into the closed orientation, the auxiliary flow path section communicates with the housing inlet port and the housing outlet port.

When the adjustable flow path does not include an auxiliary flow path section, the apparatus can be operated in the non-humidifying mode with the platform in either the opened or closed positions.

The platform can be pivoted into an opened orientation in which the act of opening the platform moves the auxiliary flow path section into the inactive position. In other words, opening the platform can disconnect the communication of the path inlet and the path outlet from the housing outlet port and the housing inlet port respectively.

In addition, when the platform is in the opened orientation, the humidification chamber may be loaded onto the housing, and the chamber inlet and the chamber outlet may be connected to the housing outlet and inlet ports respectively, thereby allowing the apparatus to be operated in a humidifying mode.

The housing may have user controls that a user can use to operate the apparatus, such as setting the mode in which the apparatus is used, or selecting and/or adjusting any operating parameters or settings of the apparatus.

The controls may include any one or a combination of: buttons, switches, dials, and/or a display screen. The display screen may be touch sensitive that may display buttons and switches that are represented on the screen for operating the apparatus.

The controls, including the display screen, may be located on the platform.

The platform may have the controls, including the display screen, which can be observed by a user when the platform is located in both the opened and closed orientations.

The platform may be located in a parallel arrangement to the housing when in the closed orientation. For example, the platform may be arranged on top of, and parallel to, the main body.

The platform may be located laterally to the main body of the housing when in the opened orientation. For example, the platform may form an acute angle to the main body when in the open position.

The platform may have an inward surface that faces toward the main body of the housing when the platform is in the closed orientation and an outward surface that faces away from the main body when in either one or both of the opened and closed orientations.

The controls, including the display screen, may be located on the outward surface of the platform. In other words, the display screen can be observed by a user when the platform is positioned in both of the opened orientation and the closed orientation.

Some of the controls may also be located on the main body of the housing. For example, the main body of the housing may include controls such as an ON/OFF switch.

The platform may be pivotally mounted to the main body by a hinge. Examples of suitable hinge mechanisms include a concealed hinge, a continuous hinge, knife hinges or spring-loaded hinges.

The controls, including the display screen, may be located on the main body.

The platform may be held in closed orientation via any suitable latching mechanisms.

The main body of the housing may have a base on which the apparatus can be seated when the apparatus is in the humidifying mode and the non-humidifying mode. That is to say, the main body of the housing may have the same orientation in both the humidifying mode and the non-humidifying mode.

The apparatus can be seated on the platform when the apparatus is the non-humidifying mode.

The apparatus may include a powered device located in the housing. The powered device may include a range of components such as the blower, a display screen and other electronic items such as user controls.

The powered device may include a heater assembly for heating the water in the humidification chamber to increase humidification of the gas stream.

The powered device may engage the humidification chamber to heat the water. The engagement between the powered device and the humidification chamber may be any one or a combination of thermal engagement, electrical power engagement, and/or an inductive power engagement.

The powered device may include an electrical connection for providing power to the humidification chamber. The humidification chamber may include a heating element which receives power from the electrical connection.

The heater assembly may be arranged on an outer face of the main body of the housing to facilitate thermal engagement between the heater assembly and the humidification chamber when the apparatus is in the humidifying mode.

The heater assembly may be mounted to a moveable wing which allows the heater plate to be engaged by the humidification chamber when the humidification chamber is located in the operating position.

The moveable wing may be or include the platform having the auxiliary flow path.

In one example, the heater assembly is mounted to an inner surface of the platform and on which the humidification chamber can be seated to thermally engage the humidification chamber and the heater assembly.

The heater assembly may have a heater plate that has a surface that heats when in use.

In one example, the heater assembly may be arranged to face outwardly from an external wall of the main body of the housing. In this example, the heater plate may be arranged in a non-movable position on the main body of the housing or in a fixed position.

The heater plate may thermally engage a thermally conductive heater base of the humidification chamber.

The powered device may include a heating element arranged in the humidification chamber and an electrical coupling for electrically connecting the heating element to a co-operating electrical coupling of the housing for powering the heating element. The electrical coupling may be any suitable connector including couplings, sockets, shielded and unshielded couplings, couplings on leads and so forth.

The electrical coupling may be connected by locating the humidification chamber into the correct position on the platform.

In an embodiment, the powered device may include an induction generator in the main body, and a co-operating heater base of the humidification chamber that heats on exposure to energy from the induction generator for heating the water in the humidification chamber. It will be appreciated that the term “induction generator” embraces a device that generators a high frequency alternating current through an electromagnet which generates a current in a target resistance material, such as the heater base of the humidification chamber, which in turn generates heat in the humidification chamber. An advantage in heating the water in the humidification chamber using induction is that the efficiency of heating the water is not dependent on conductive thermal engagement with the humidification chamber.

The apparatus may include a coupling assembly.

The coupling assembly may couple together the main body of the housing and the humidification chamber when the apparatus is in the humidifying mode.

The coupling assembly may couple together the housing and the platform in the active position when the apparatus is in the non-humidifying mode. That is, with the platform in the closed orientation.

The coupling assembly may couple together the housing and the auxiliary flow path when the apparatus is in the non-humidifying mode.

The coupling assembly may couple together the humidification chamber and the platform when the apparatus is in the humidifying mode, that is, with the platform in the opened orientation.

The coupling assembly may include a first formation on a body of the humidification chamber, and a second formation on the main body of the housing, and the first and second formations inter-fit when the humidification chamber is located in the operating position.

The first and second formations may be arranged to assist in aligning the chamber inlet and the chamber outlet with the housing inlet port and the housing outlet port respectively.

The coupling assembly may include a third formation on the platform.

The coupling assembly may include: a first latching portion on the body of the humidification chamber and a co-operating second latching portion on the main body of the housing that can releasably engage the first latching portion.

The coupling assembly may include a third latching portion on the platform and/or the auxiliary flow path that can releasably engage the second latching portion.

The first latching portion can releasably engage the second latching portion when the apparatus is in the humidifying mode.

The second latching portion can releasably engage the third latching portion when the apparatus is in the non-humidifying mode.

The coupling assembly may include a fourth latching portion on the body of the humidification chamber that can be releasably engage the third latching portion on the platform.

The fourth latching portion may be located on an upper portion of the humidification chamber and the third latching portion may be located toward an outer end of the platform.

The fourth latching portion may be located on a lower portion of a body of the humidification chamber and the third latching portion may be located adjacent to the hinge that mounts the platform to the main body. The third latching portion and the fourth latching portion releasably engage when the apparatus is in the humidifying mode.

If the apparatus includes an auxiliary flow path section, and when the apparatus is in the non-humidifying mode, the platform may be located in the closed orientation which also locates the auxiliary flow path section in an active position.

The coupling assembly may also include a locking mechanism for securing the platform at an angled orientation to the main body of the housing. For instance, at a closed orientation or the opened orientation. The locking mechanism may be adjustable to allow the platform to be releasably secured at multiple angles of orientation to the main body when in the opened orientation.

If the apparatus does not include an auxiliary flow path section, the platform can be located in the opened orientation when apparatus is in the non-humidifying mode.

The first, second, third and fourth latching portions, and the locking mechanism, may comprise any co-operating connectors including: a sliding connector, a screw connector, a bayonet connector, a ball and socket connector, a magnet connector, a push-latch connector, a spring latch connector, a snap fit connector, or a connector having a male-female interference fit, toggle connector, a gravity connector.

The coupling assemblies may have a sliding coupling that allows the humidification chamber to slide relative to the main body into the operative position. The humidification chamber may also slide relative to the main body when being removed from the main body into the inoperative position.

The sliding coupling may include a projection that is can be received by a recess, and the projection can move along the recess when sliding the humidification chamber relative to the main body.

The projection and the recess may, for example, be one or more of the following: i) a tongue and groove arrangement, ii) a T-shaped flange that is received by a co-operating T-shaped slot, iii) a pair of rails and carriage that fits between the rails; or iv) a undercut that receives a rib. The projection may be located on the humidification chamber and the recess on the main body, and vice versa.

The adjustable flow path, in its various configurations, is ideally sealed. The terms "seal", "sealed", "sealed connection" or variations thereof refers to a gas tight connection which prevents any substantial change in either the flow rate or pressure of the gash dream is leakage from the sealed connection is minimised.

If the apparatus includes the auxiliary flow path section, the path inlet and the path outlet of the auxiliary flow path section can form a sealed connection to the housing outlet port and the housing inlet port respectively when the apparatus is in the non-humidifying mode.

For example, the sealed connection may include the path inlet and the path outlet being received within the housing outlet port and the housing inlet port respectively. In another example, the sealed connection may include the housing outlet port and the housing inlet port being received within the path inlet and the path outlet respectively.

It is also possible that the path inlet may seal with the housing outlet port without one receiving the other. It is also possible that the path outlet may seal with the housing inlet port without one receiving the other.

The chamber inlet and the chamber outlet can also form a sealed connection with the housing outlet port and the housing inlet port respectively, when the apparatus is in the humidifying mode.

The conduit outlet port, including either the chamber conduit port and/or the housing conduit port may form a seal connection with the user conduit.

For example, the sealed connection may include the housing outlet port and the housing inlet port being received within the chamber inlet and the chamber outlet respectively. In another example, the sealed connection may include the chamber inlet and the chamber outlet being received within the housing outlet port and the housing inlet port respectively. In further examples there may be a combination of the above arrangements.

It is also possible that the chamber inlet may seal with the housing outlet port without one receiving the other. It is also possible that the chamber outlet may seal with the housing inlet port without one receiving the other.

The term "sealed connection" refers to a gas tight connection that prevents any substantial change in either the flow rate or pressure of the gas stream, as leakage from the sealed connection is minimised.

For example, the sealed connection may include the housing outlet port and the housing inlet port being received within the chamber inlet and the chamber outlet respectively. In another example, the sealed connection may include the chamber inlet and the chamber outlet being received within the housing outlet port and the housing inlet port respectively. In further examples there may be a combination of the above arrangements.

It is also possible that the chamber inlet may seal with the housing outlet port without one receiving the other. It is also possible that the chamber outlet may seal with the housing inlet port without one receiving the other.

The apparatus may include at least one locator formation that provides alignment of the chamber inlet with housing outlet port, and alignment of the chamber outlet with the housing inlet port, when the apparatus is in the humidifying mode.

For example, an outer wall of the humidification chamber may be seated in a channel formation of the platform.

In another example, a bottom wall of the humidification chamber may have a heater base and an apron extending downwardly from the heater base, the apron fitting about the sidewall of the heater assembly. The apron of the humidification chamber may be sized so that the heater assembly is frictionally fitted within the apron.

In an example, the auxiliary flow path may be flow connected to the housing outlet port and the housing inlet port and a valve may be operable to selectively allow the gas stream to be conveyed along the auxiliary flow path.

In an example, the auxiliary flow path may form part of the housing in a fixed position. The valve may be operable to open and close the auxiliary flow path independently of the status or position of the humidification chamber.

An embodiment of the present invention relates to an apparatus for providing respiratory assistance to a user, the apparatus being operable in a humidifying mode with a humidification chamber, and a non-humidifying mode, wherein the apparatus includes:

a blower for generating a gas stream;

an adjustable flow path for the gas stream to which the user conduit can be connected;

a housing having at least part of the adjustable flow path that extends from the blower to a housing outlet port; and a platform that is operably connected to the housing so that the platform can move between:

i) an opened orientation in which the humidification chamber can be located in the operating position on the housing and in turn operates the apparatus is in the humidifying mode; and ii) a closed orientation in which the humidification chamber is separate from the housing and in turn operates the apparatus in the non-humidifying mode.

The apparatus described in the paragraph immediately above may also include any one or a combination of the features described herein. For example, the platform may have user controls for operating the apparatus. The user controls may also include controls located on the housing.

An embodiment of the present invention relates to an apparatus for providing respiratory assistance to a user via a user conduit, the apparatus being operable in a humidifying mode and a non-humidifying mode, wherein the apparatus includes:

a blower for generating a gas stream;

an adjustable flow path for the gas stream to which the user conduit can be connected;

a housing having a section of the adjustable flow path, the portion extending from the blower to a housing outlet port;

a removeable humidification chamber having a chamber inlet which can be moved between:

i) an operating position in which the chamber inlet communicates with the housing outlet port to convey the gas stream through the humidification chamber, and therefore the humidification chamber is included in the adjustable flow path which operates the apparatus in the humidifying mode, and ii) a non-operating position in which communication between the chamber inlet and the housing outlet port is broken, and therefore the humidification chamber is excluded from the adjustable flow path which operates the apparatus in the non-humidifying mode.

The apparatus described in the paragraph immediately above may also include any one or a combination of the features described herein. For example, the apparatus may include a locking mechanism for securing the platform in the opened orientation and the closed orientation. The locking mechanism may also be operable to secure the platform at various positions between the opened orientation and the closed orientation. That is to say, the locking mechanism may be operable to secure the platform, and thus the user controls at an angle to the housing when they humidification chamber is separate from the housing.

An embodiment of the present invention relates to an apparatus for providing respiratory assistance to a user via a user conduit, the apparatus being operable in a humidifying mode and a non-humidifying mode, wherein the apparatus includes:

a blower for generating a gas stream;

a housing having a housing outlet port that is in communication with the blower, and a housing inlet port that can communicate with the user conduit;

a humidification chamber having a chamber inlet and a chamber outlet, the humidification chamber being movable and able to be located in an operating position in which the chamber inlet communicates with the housing outlet port and the chamber outlet communicates with the housing inlet port to convey the gas stream through the humidification chamber when the apparatus is in the humidifying mode; and an auxiliary flow path that is operably connected to the housing so as to move between:

i) an active position in which the auxiliary flow path communicates with the housing outlet port and the housing inlet port to convey the gas stream therebetween when the apparatus is in the non-humidifying mode, and ii) an inactive position in which the auxiliary flow path is remote from the housing outlet port and the housing inlet port so the humidification chamber can be located in the operating position when the apparatus is in the humidifying mode.

An embodiment of the present invention relates to an apparatus for providing respiratory assistance to a user via a user conduit, the apparatus being operable in a humidifying mode and a non-humidifying mode, wherein the apparatus includes:

a blower for generating a gas stream;

a housing having a housing outlet port that is in communication with the blower, a housing inlet port that can communicate with the gas stream conduit, and the housing can be connected to a power source to receive power;

a humidification chamber for containing an amount of water and having a chamber inlet and a chamber outlet, and the humidification chamber can be located in an operating position in the humidifying mode in which the chamber inlet communicates with the housing outlet port and the chamber outlet communicates with the housing inlet port to convey the gas stream through the humidification chamber; and an auxiliary flow path that can be located in an operating position in the non-humidifying mode in which the auxiliary flow path communicates with the housing inlet port and the housing outlet port to convey the gas stream therebetween; and a powered device that heats water in the humidification chamber when the apparatus is in the humidifying mode, and the powered device can be powered by the power source connected to the housing.

The apparatus described in the paragraph immediately above may also include any one or a combination of the features described herein. For example, the platform may have user controls for operating the apparatus. The user controls may also include controls located on the housing.

An embodiment of the present invention relates to an apparatus for providing respiratory assistance to a user, the apparatus being operable in a humidifying mode and a non-humidifying mode, wherein the apparatus includes:

a blower for generating a gas stream;

a housing having a housing outlet port that is in communication with the blower, and a housing inlet port;

a user conduit that communicates with the housing inlet port for delivering the gas stream to a user;

a humidification chamber having a chamber inlet and a chamber outlet, the humidification chamber being movable and able to be located in an operating position in which the chamber inlet communicates with the housing outlet port and the chamber outlet communicates with the housing inlet port to convey the gas stream through the humidification chamber when the apparatus is in the humidifying mode; and an auxiliary flow path that is operably connected to the housing so as to move between:

i) an active position in which the auxiliary flow path communicates with the housing outlet port and the housing inlet port to convey the gas stream therebetween when the apparatus is in the non-humidifying mode, and ii) an inactive position in which the auxiliary flow path is remote from the housing outlet port and the housing inlet port so the humidification chamber can be located when the apparatus is in the operating position in the humidifying mode.

An embodiment of the present invention relates to an apparatus for providing respiratory assistance to a user, the apparatus being operable in a humidifying mode in which a humidification chamber having a chamber inlet and a chamber outlet can be located in an operating position on the apparatus, and a non-humidifying mode, wherein the apparatus includes:

a blower for generating a gas stream;

a housing having a housing outlet port that is in communication with the blower, and a housing inlet port that can communicate with the gas stream conduit;

an auxiliary flow path that is operably connected to the housing so as to move between:

i) an active position in which the auxiliary flow path communicates with the housing outlet port and the housing inlet port to convey the gas stream therebetween in the non-humidifying mode, and ii) an inactive position in which the auxiliary flow path is remote from the housing outlet port and the housing inlet port which allows the humidification chamber to be located in the operating position in the humidifying mode.

An embodiment of the present invention relates to an apparatus for providing respiratory assistance to a user via a gas stream conduit, the apparatus being operable in a humidifying mode in which a humidification chamber can be located in an operating position on the apparatus and a non-humidification mode, wherein the apparatus includes:

a blower for generating a gas stream;

a housing having a housing outlet port that is in communication with the blower; and a heating assembly that is moveable relative to the housing, and (when the apparatus is) in the humidification mode, the heating assembly can be located in an operating position in which a humidification chamber can engaged by the heating assembly, and in the non-humidification mode, the heating assembly can be located in a stowed position in which the humidification chamber is unable to be loaded on the heating element.

The phrase, "the heating assembly being located in a stowed position . . . " in the preceding paragraph or equivalent phrases elsewhere in this specification, embraces the heating assembly being connected to the housing and disposed adjacent to the housing in a manner that either reduces the size of the apparatus and/or positions the heating assembly in a non-operable location. For example, the heating element in the operating position is moved away from the housing to allow engagement with the humidification chamber and is moved toward the housing so humidification chamber is unable to engage in the stowed position. In the stowed position, the apparatus may be smaller in footprint or smaller in some other dimension compared to when the heating assembly is in the operating position.

The apparatus in the paragraph immediately above may include any one or a combination of the feature of the other apparatuses described herein. For example, the apparatus may include a humidification chamber having a chamber inlet and a chamber outlet, in which the humidification chamber is movable and can be located in an operating position in which the chamber inlet communicates with the housing outlet port and the chamber outlet communicates with the housing inlet port to convey the gas stream through the humidification chamber when the apparatus is in the humidifying mode.

An embodiment of the present invention relates to a method of operating an apparatus to provide respiratory assistance to a user, in which the apparatus can be operated in a humidifying mode and a non-humidifying mode, and the method includes:

providing a housing having a housing outlet port that is in communication with a blower, and housing inlet port that can communicate with the gas stream conduit;

operating a blower to generate a gas stream;

locating a humidification chamber having a chamber inlet and a chamber outlet in an operating position in which the chamber inlet communicates with the housing outlet port and the chamber outlet communicates with the housing inlet port and conveying the gas stream through the humidification chamber in the humidifying mode; and moving an auxiliary flow path between:

i) an active position in which the auxiliary flow path communicates with the housing outlet port and the housing inlet port and conveys the gas stream therebetween in the non-humidifying mode, and ii) an inactive position in which the auxiliary flow path is remote from the housing outlet port and the housing inlet port which allows the humidification chamber to be located in the operating position in the humidifying mode.

The method may include retaining the gas stream conduit in communication with the gas stream outlet port in both the humidifying mode and the non-humidifying mode.

The method described in two paragraphs immediately above may also include any one or a combination of the features of the apparatus described herein.

BRIEF DESCRIPTION OF THE DRAWINGS

A preferred embodiment of the present invention will now be described with reference to the company drawings which are summarised as follows.

FIGS. 8 and 9 show the apparatus in two operating orientations in the non-humidifying mode.

FIG. 14 is a table illustrating the method steps of operating an apparatus to provide respiratory assistance to a user, in which the method includes operating the apparatus in a humidifying mode and a non-humidifying mode.

DETAILED DESCRIPTION

Figure 1:
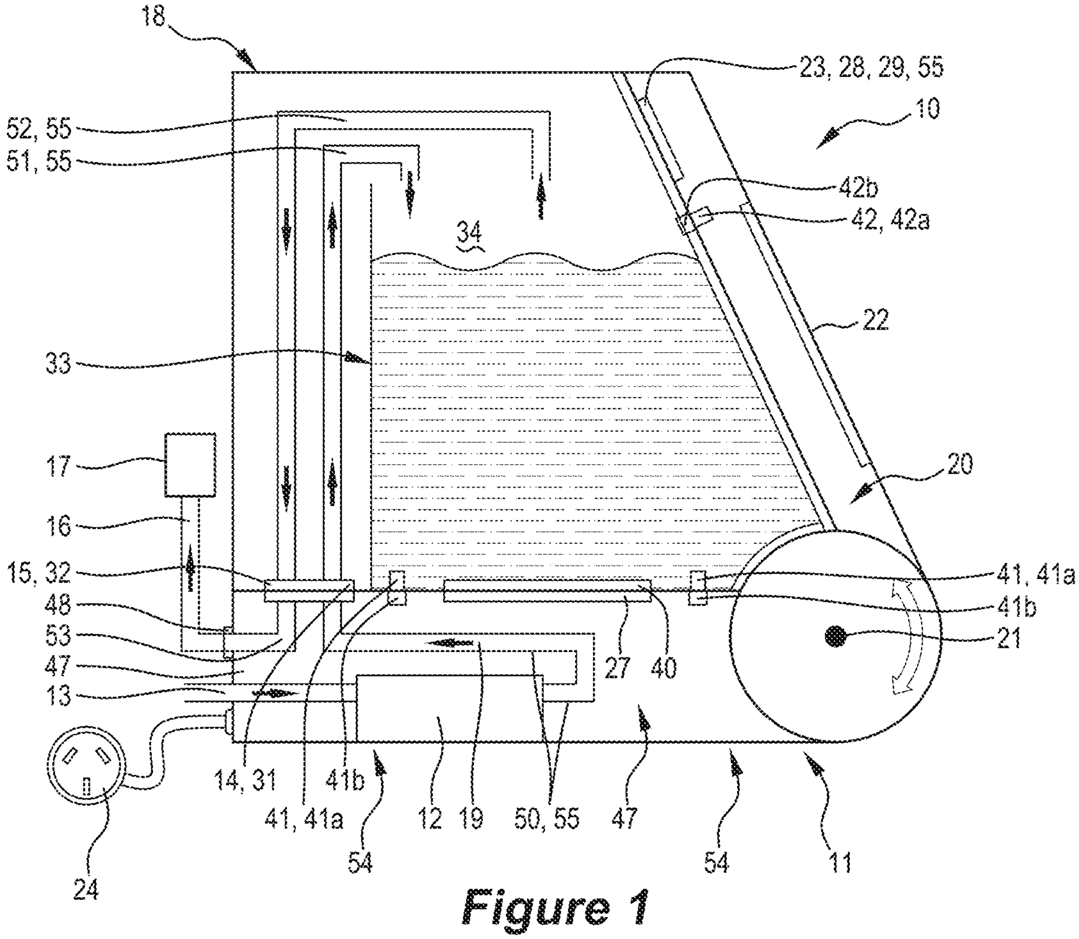
FIG. 1 is a schematic view of an apparatus according to an embodiment in a humidifying mode. The apparatus includes a removable humidification chamber that is located in an operating position, an adjustable flow path with arrows indicating the direction of flow of a gas stream along the flow path and a platform located in an opened orientation, the platform including a display screen and an auxiliary flow path section.

A preferred embodiment of the present invention will now be described in the following text which includes reference numerals that correspond to features illustrated in the accompanying Figures. To maintain clarity of the Figures, however, not all reference numerals are included in each Figure.

With reference to FIGS. 1 to 6B, the apparatus 10 includes a housing 11 having a main body 47 and a platform 20 that is hinged to the main body 47 by hinge mechanism 21, and a blower 12 located within the main body 47 of the housing 11 for generating a gas stream. The blower 12 draws ambient air into the blower through an air inlet filter 13. If required, supplemental oxygen can be added to the ambient air to enrich the gas stream with oxygen; the supplemental oxygen can be added at any suitable part of the gas stream, e.g. before the blower, after the blower, after the humidifier, or at the patient interface. The housing 11 has a housing outlet port 14 in the main body 47 that is in communication with an outlet of the blower 12, and a housing inlet port 15 in the main body 47 that is in communication with a user conduit 16 that supplies the gas stream to a user interface 17. The apparatus 10 also includes a removable humidification chamber 18 containing an amount of water in a water tub 33 for humidifying the gas stream 19, and an adjustable flow path 55 that can change configuration depending on whether the apparatus 10 is operating in a humidifying mode or a non-humidifying mode.

The platform 20 has a user controls in the form of display screen 22, such as an LCD, plasma or other display. Ideally the display screen 22 is a touchscreen having control buttons.

The main body 47 of the housing 11 also has a base 54 on which apparatus 10 seats in both the humidifying mode and the non-humidifying mode.

Figure 2A:
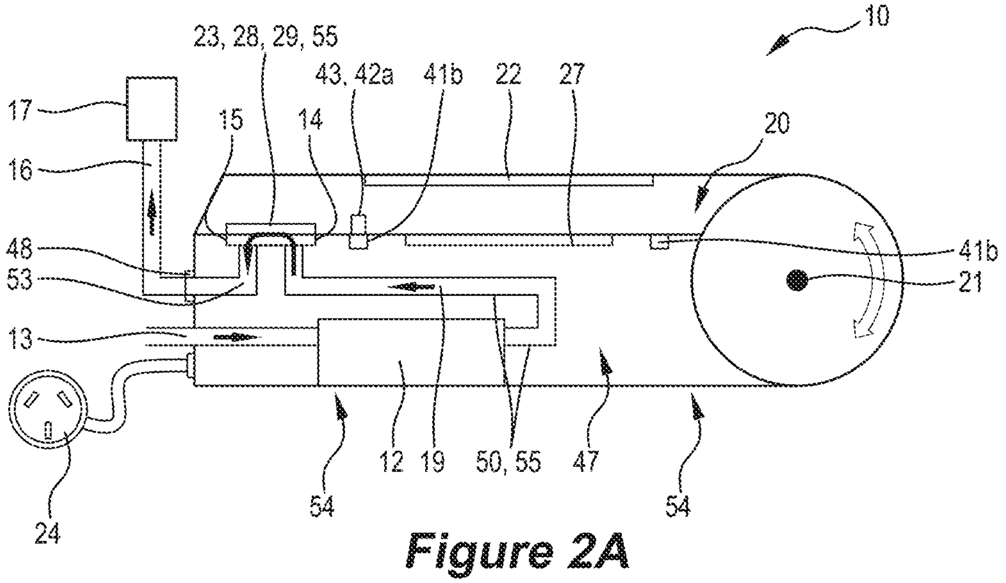
FIG. 2A is a schematic view of the apparatus shown in FIG. 1 in a non-humidifying mode, in which the humidification chamber is separate from the apparatus so as not to form part of the flow path, and the platform in a closed orientation.
Figure 2B:
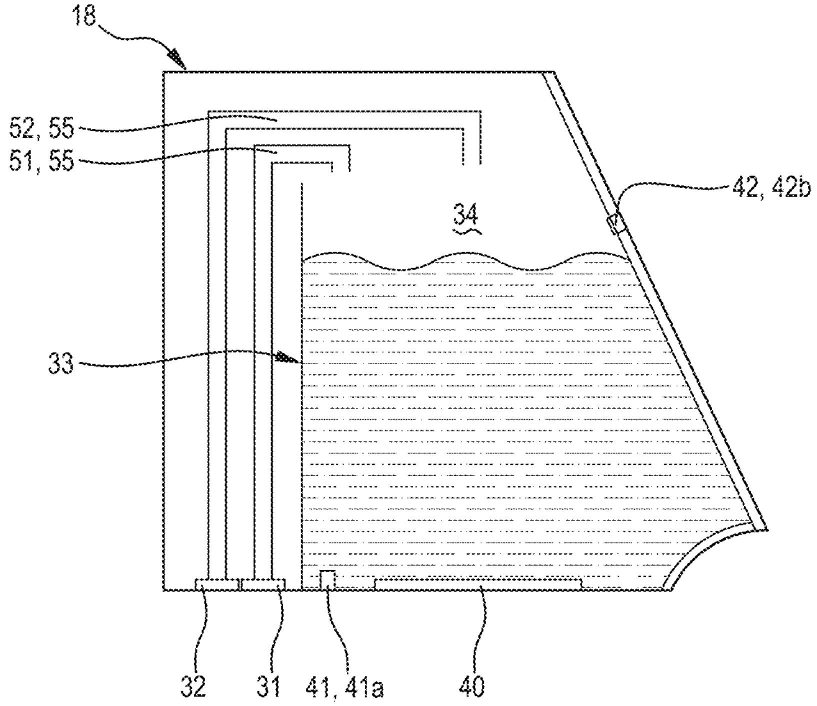
FIG. 2B is a schematic view of the removable humidification chamber shown in FIG. 1 that has been separated from the apparatus.
Figure 3:
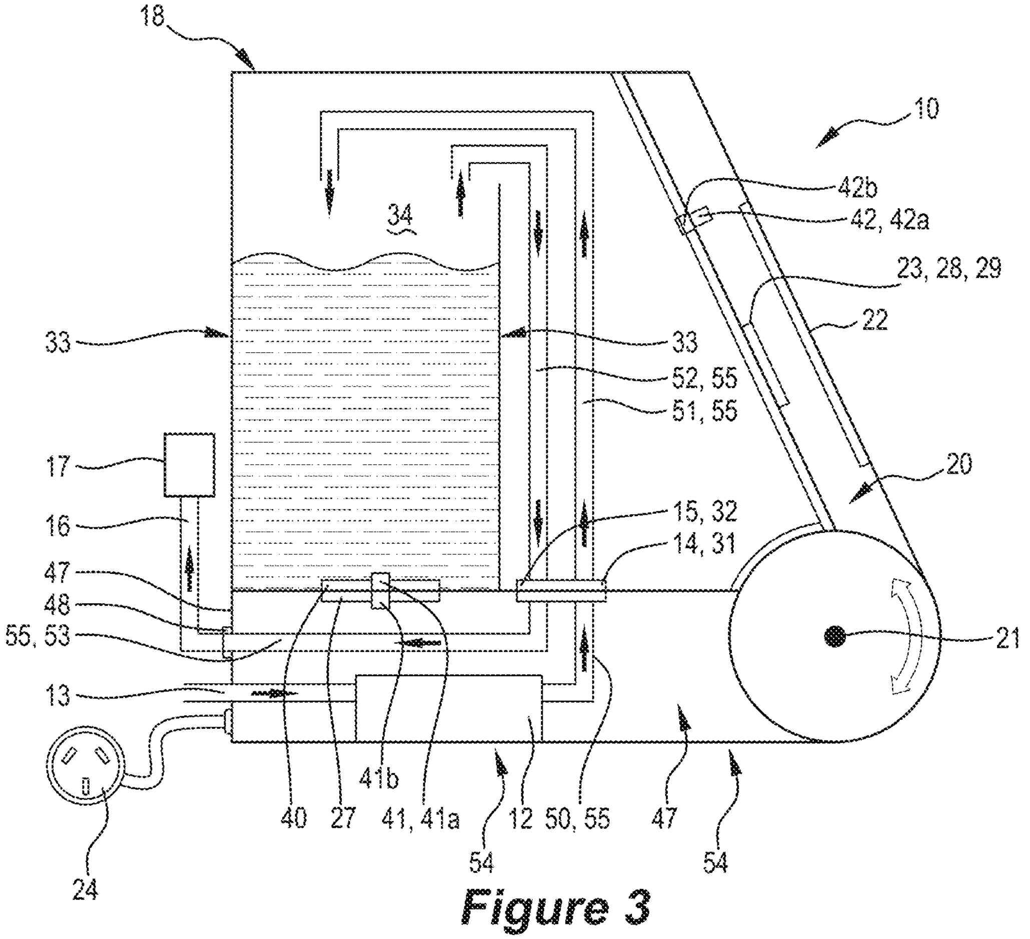
FIG. 3 is a schematic view of an apparatus according to another embodiment in a humidifying mode. Like the embodiment shown in FIG. 1, the apparatus includes a removable humidification chamber that is located in an operating position, an adjustable flow path with arrows indicating the direction of flow of a gas stream along flow path, and the platform including a display screen and an auxiliary flow path section arranged adjacent to a hinge mounting of the platform.
Figure 4A:
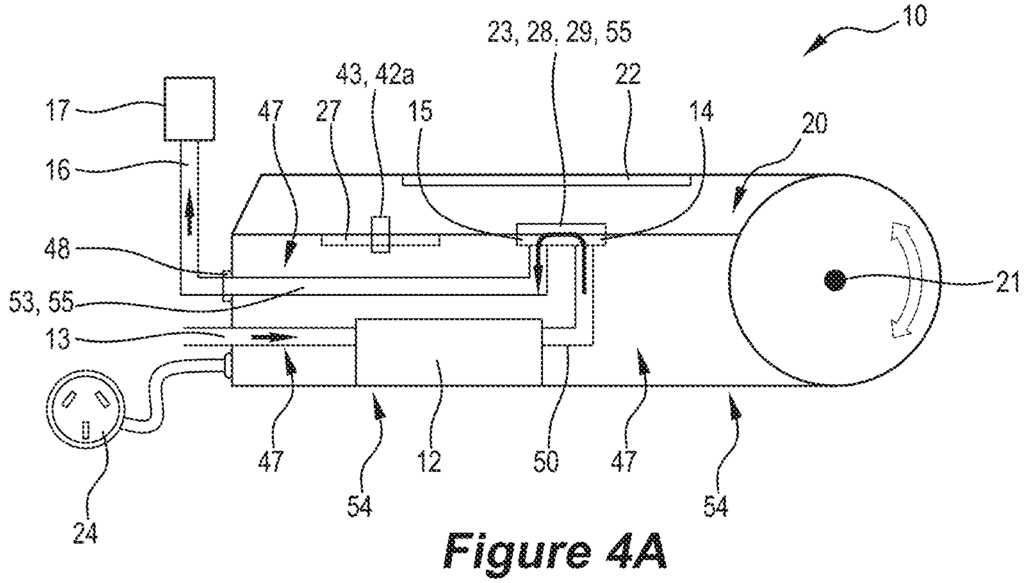
FIG. 4A is a schematic few of the apparatus shown in FIG. 3 in a non-humidifying mode, in which the humidification chamber is separate from the apparatus so as not to form part of the flow path, and the platform is in a closed position to locate the auxiliary flow path section in an active position.
Figure 4B:
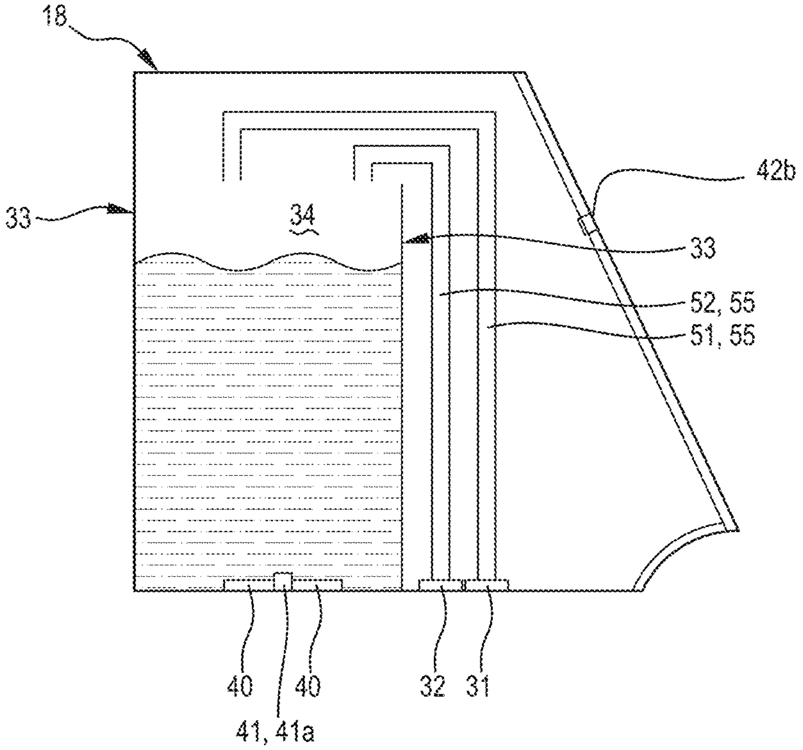
FIG. 4B is a schematic view of the removable humidification chamber shown in FIG. 3 that has been separated from the apparatus.
Figure 5:
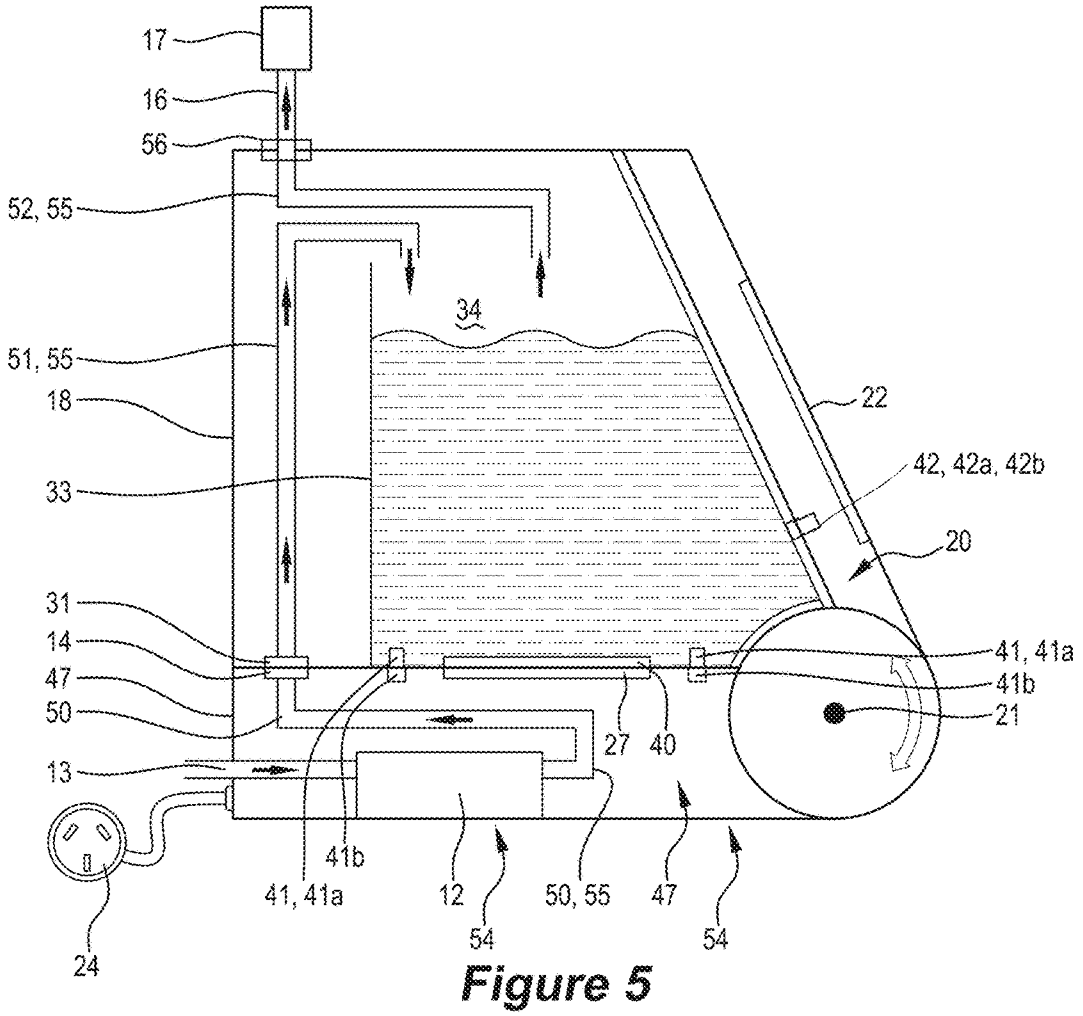
FIG. 5 is a schematic view of an apparatus according to another embodiment in a humidifying mode. The apparatus includes a removable humidification chamber that is located in an operating position, and an adjustable flow path with arrows indicating the direction of flow, and the platform including a display screen.

In the case of the embodiment shown in FIGS. 1 to 4B, the platform 20 carries an auxiliary flow path section 23, and can be pivoted into an opened orientation, best shown in FIGS. 1, 3 and 5, for accommodating the humidification chamber 18 on the main body 47 of the housing 11. The auxiliary flow path section 23 is also located in an inactive position when the platform 20 is positioned in the opened orientation.

In the case of the embodiment shown in FIGS. 5 and 6, the platform 20 is not required to include an auxiliary flow path section 23, but an auxiliary flow path section 23 can still be included as an option.

Figure 6A:
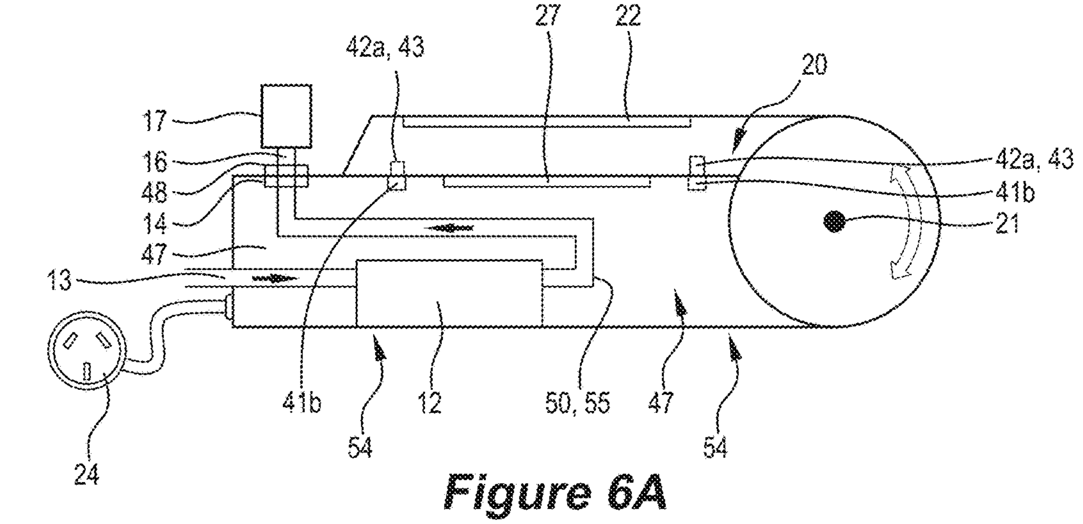
FIG. 6A is a schematic view of an apparatus shown in FIG. 5 in a non-humidifying mode, in which the humidification chamber is separate from the apparatus so as not to form part of the flow path, and the platform, including a display screen is located in a closed orientation. The platform can be located in either the closed or opened positions when being operated in the non-humidifying mode.

In the humidifying mode, the platform 20 is pivoted into the opened orientation and the humidification chamber 18 is loaded or seated on the main body 47 of the housing 11, see FIGS. 1, 3 and 5. FIGS. 2A, 4A, 6A illustrate the apparatus 10 in the non-humidifying mode, in which the humidification chamber 18 is separate from the platform 20 and the platform 20 is pivoted into a closed orientation. In the case of the embodiment shown in FIGS. 1 to 4B, the auxiliary flow path section 23 is active for conveying the gas stream 19 when the apparatus is in the non-humidifying mode.

A benefit of the apparatus 10 shown in all of the Figures is that it can be switched between the humidifying mode and the non-humidifying mode quickly and easily by a user who may have limited hand dexterity. Switching the apparatus between modes can be achieved by fitting or removing the humidification chamber 18 and pivoting the platform 20 between opened and closed orientations. It is believed that such actions are comparatively intuitive and easy for a user.

The adjustable flow path 55 of the embodiment illustrated in FIGS. 1 to 4B has a return configuration in both the humidifying mode and the non-humidifying mode. As mentioned above, when the apparatus 10 is in the non-humidifying mode, the auxiliary flow path section 23 is located in an active position and characterizes the return configuration by the gas stream 19 passing though the auxiliary flow path section 23 back to the main body 47 of the housing 11. FIGS. 5 and 6 illustrate an embodiment having an adjustable flow path 55 that has a non-return configuration in both the humidifying mode and the non-humidifying mode, and does not include the auxiliary flow path section 23.

In the case of FIGS. 1 to 4A, the adjustable flow path 55 comprises a fixed section 50 of ducting extending from, and includes, an outlet of the blower 12 to the housing outlet port 14. The direction of flow of the gas stream 19 in the ducting is indicated by arrows. The humidification chamber 18 has a chamber inlet 31 that connects to the housing outlet port 14, and the adjustable flow path 55 includes: a first passageway for the gas stream extending from the chamber inlet 31 to a water tub 33, and a second passageway for conveying the gas stream 19 extending from the water tub 33 to a chamber outlet 32. When the apparatus 10 is in the non-humidifying mode, the humidification chamber 18 is removed from the main body 47 and the first and second passageways 51 and 52 do not form part of the adjustable flow path 55. When the apparatus 10 is in the humidifying mode, the humidification chamber 18 is loaded onto the main body 47 of the apparatus 10, and the first and second passageways 51 and 52 form part of the adjustable flow path 55.

The adjustable flow path 55 of the embodiments in FIGS. 1 to 4A further include a removable section 53 that extends from, and includes, the housing inlet port 15 to a housing conduit port 48 for connecting to a user conduit 16 that conveys the gas stream 19 to a user interface 17. The removable section 53 therefore conveys the gas stream when humidified, and the removable section 53 can be replaced and/or cleaned in accordance with a suitable hygiene regime.

In addition, the adjustable flow path 55 of the embodiments illustrated in FIGS. 1 to 4A includes an auxiliary flow path section 23 that has a passageway including a path inlet 28 and a path outlet 29 that forms part of, or is attached to, the platform 20. The auxiliary flow path 23 has an inactive position in which the auxiliary flow path section 23 does not form part of the adjustable flow path 55 and corresponds to when the platform 20 is not in the closed orientation, i.e., an opened orientation. For example, when the platform 20 is pivoted fully opened, the humidification chamber 18 can be loaded onto the housing 11 as shown in FIGS. 1 and 3.

In the case of the embodiment illustrated in FIGS. 1 to 4A, the auxiliary flow path section 23 also has an active position which forms part of the adjustable flow path 55 when the platform 20 is pivoted into the closed orientation and the path inlet 28 connects to the housing outlet port 14 and the path outlet 29 connects to the housing inlet port 15. The auxiliary flow path section 23 is therefore located in the active position only when the apparatus 10 is being operated in the non-humidifying mode.

The housing outlet port 14 and the housing inlet port 15 of the embodiment in FIGS. 1, 2A and 2B are located on the main body 47 of the housing 11 at a position that is oppositely disposed to the hinge mechanism 21. In comparison, the housing outlet port 14 and the housing inlet port 15 are located adjacent to the hinge mechanism 21 in FIGS. 3, 4A. Similarly, the auxiliary flow path section 23 is arranged either adjacent to the hinge mechanism 21, as shown in FIGS. 3 and 4A, or at an outer end of the platform, as shown in FIGS. 1 and 2A, so as to facilitate engagement with the housing outlet port 14 and the housing inlet port 15 when the platform 20 is in the closed orientation.

A further consideration with the embodiments of FIGS. 1 to 4A, is that the auxiliary flow path 23 is located on the platform 20 to allow the auxiliary flow path 23 to connect to the housing inlet and outlet ports 14 and 15 and compliment the size of the humidification chamber 18. In the case of the embodiment in FIGS. 3 and 4A, the auxiliary flow path 23 is adjacent to the hinge mechanism 21, and hence the auxiliary flow path 23 can be readily arranged on the platform 20 to connect to the housing outlet and inlet ports 14 and 15. However, in the case of the embodiment in FIGS. 1, 2A and 2B, although not shown in the figures the height dimension in a direction from the hinge mechanism 21 to the outer end of the platform 20 may be adjustable, for example by a suitable sliding or folding adjustment mechanism. By incorporating an adjustment mechanism, the platform 20 may extend and retract to allow an outer end of the platform 20 to align flush with a top wall of the humidification chamber 18 as shown in FIG. 1, and allow the auxiliary flow path 23 to connect to the housing inlet and outlet ports 14 and 15 in the non-humidification mode.

Although not shown, the adjustable flow path 55 of the embodiment of FIGS. 1 to 4A may include a valve that can be switched to direct the gas stream 19 from the blower 12 to either one of: i) the housing outlet port 14; or ii) a housing conduit port 48 of the housing 11. The valve may be provided instead of the auxiliary flow path 23. The valve may be switched by the user, the apparatus 10 may include an actuator for switching the valve, for example, when the platform 20 is moved between the opened and closed orientations.

The user conduit 16 of the embodiment illustrated in FIGS. 1 to 4A remains connected to the same housing conduit port 48 when the apparatus 10 is switched between the humidifying mode and the non-humidifying mode. A benefit of the embodiment in FIGS. 1 to 4A, is that the apparatus 10 can be switched between the humidifying mode, as shown in FIGS. 1 and 3, and the non-humidifying mode, as shown in FIGS. 2A and 4A, quickly and easily by a user who may have limited hand dexterity. Switching the apparatus 10 between modes can be achieved by fitting or removing the humidification chamber 18 and pivoting the platform 20 between opened and closed orientations. It is believed that such actions are comparatively intuitive and easy for a user. Moreover, the user is not required to disconnect and reconnect the user conduit 16 to the housing conduit port 48.

Figure 6B:
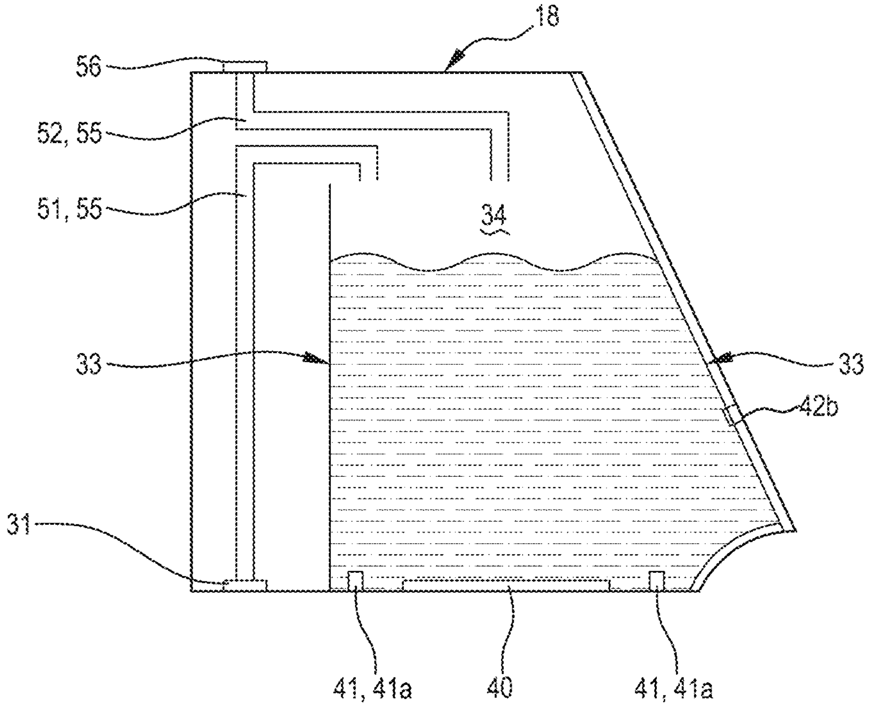
FIG. 6B is a schematic view of the removable humidification chamber shown in FIG. 5 that has been separated from the apparatus.

In comparison, the adjustable flow path 55 of the embodiment shown in FIGS. 5, 6A and 6B is a non-return configuration and does not require an auxiliary flow path section 28. Rather, a fixed section 50 of the adjustable flow path 55 extends from an outlet of the blower 12 that is flow connected to the housing outlet port 14. The direction of flow of the gas stream 19 is indicated by arrows. The adjustable flow path 55 includes a chamber inlet 31 on the humidification chamber 18 that connects to the housing outlet port 14, and a first passageway 51 for conveying the gas stream from the chamber inlet 31 to a water tub 33. The adjustable flow path 55 also includes a second passageway 52 for the gas stream 19 from the humidification chamber 18 to a housing conduit port 48 positioned on the humidification chamber 18 without the humidified gas stream 19 returning to the main body 47 of the housing 11.

When the apparatus 10 of FIG. 5 is operated in the humidifying mode, the user conduit 16 is connected directly to a housing conduit port 48 on the humidification chamber 18.

When the apparatus 10 of FIGS. 5 and 6A is operated in the non-humidifying mode, the user conduit 16 is connected directly to the housing conduit port 48 which is the housing outlet port 14.

An advantage of each of the embodiments shown in FIGS. 1 to 6B is that main body 47 of the apparatus 10 sits on a base 54 with the main body 47 in the same orientation in both the humidifying mode and in the non-humidifying mode.

The display screen 22 is arranged on the outer surface of the platform 20 and can be seen by the user in both the opened and closed orientations. Although not shown in the drawings, one of the advantages of the embodiment shown in FIGS. 5 and 6A is that when the apparatus 10 is being used in the non-humidifying mode, it is not necessary that the platform 20 be located in the fully closed orientation. Moreover, during the non-humidifying mode, the platform of the apparatus shown in FIGS. 5 and 6A may be located in either the opened orientation, the closed orientation, or any intermediate orientation therebetween. This may be beneficial as the user may be able to adjust the angle of the platform to see the display more easily, even during operation of the apparatus.

The hinge mechanism 21 that pivotally connects the platform 20 to the main body 47 of the housing 11 may be any suitable hinge mechanism. Examples of a suitable hinge mechanism include a concealed hinge, a continuous hinge, a knife hinge, or a spring-loaded hinge. Ideally, the hinge mechanism has a controller that controls the rate at which the platform 20 moves from the closed orientation to the opened orientation. Although not shown in the Figures, the controller may include one or more of: a torque spring, gas struts, coiled springs, or hydraulic mechanisms.

Although not shown in the Figures, a latch may releasably secure the platform 20 in the opened orientation. The latch can be released to allow the platform to be moved from the opened orientation to the closed orientation.

The humidification chamber 18 may be coupled to the housing 11 when the apparatus 10 is in the humidifying mode by a first coupling assembly 41. Specifically, as shown in FIGS. 1, 3 and 5, the first coupling assembly 41 releasably connects a bottom region of the humidification chamber 18 to the main body 47 of the housing 11. The first coupling assembly 41 includes: a first latching portion 41*a* on the bottom region of the humidification chamber 18 which engages a second latching portion 41*b* on the main body 47 of the housing 11.

Similarly, the humidification chamber 18 may also be coupled to the platform 20 when the apparatus 10 is in the humidifying mode by a second coupling assembly 42. Specifically, as shown in FIGS. 1, 3 and 5, the second coupling assembly 42 releasably connects the platform 20 to the humidification chamber 18. The second coupling assembly 42 includes a third latching portion 42*a* on the platform 20 which engages a fourth latching portion 42*b* on the humidification chamber 18, as shown in FIGS. 1 and 3.

When the apparatus 10 is in the non-humidifying mode, the platform 20 is pivoted onto the main body 47 of the housing 11 on the closed orientation, and a third coupling assembly 43 may secure the platform 20 closed with the auxiliary flow path section 23 in the active position. As can be seen in FIGS. 2, 4 and 6, the third coupling assembly 43 may comprise the third latching portion 42*a* of the platform 20 engaging the second latching portion 41*b* on the main body 47 of the housing 11.

Examples of different mechanisms suitable for coupling and locating the humidification chamber to the housing, coupling and locating the platform to the humidification chamber, and coupling the platform to the housing when the platform is in the closed orientation, include: a sliding connector, a screw connector, a bayonet connector, a magnet connector, a push-latch connector, or a male-female interference fit connector.

The housing 11 is connected to a power source via an electrical coupling 24 which powers the blower 12 and other components. If required, the apparatus 10 can include a rechargeable battery for powering the apparatus 10 when mains electricity is not available.

The apparatus 10 includes a powered device having a heater assembly that has a heater plate 27 fixed to, or separable from, the main body 47 of the housing 11. The heater plate 27 has a planar surface that is heated using electrical power and may have any suitable structure, include a biasing device (not illustrated in the Figures) that urges the heater plate 27 away from a base of the main body 47 of the housing 11, such that when the humidification chamber 18 is loaded onto the main body 47, the heater plate 27 presses against the humidification chamber 18 to enhance thermal engagement therebetween. The humidification chamber 18 also has a heater base 40 in the form of a metallic or aluminium plate for transferring heat to water in the water tub 33.

In other embodiments, the powered device may include an induction device that heats the heater base 40 or an alike structure of the humidification chamber 18. In yet another embodiment, the powered device apparatus may include a heating element position inside the water tub 33 of the humidification chamber 18, and the humidification chamber 18 and the main body 47 of the housing 11 have co-operating electrical couplings for powering the heating element. The heating element may be permanently fixed in position in the water tub 33, or removeable from the water tub 33.

The platform 20 may have an inner surface that faces toward the main body 47 of the housing 11 when the platform 20 is in the closed orientation and an outer surface that faces away from the main body 47 when in either one or both of the opened and closed orientations. Although not shown in detail in the Figures, the inner surface of the platform 20 includes a recess that at least partly receives the heater plate 27 when the platform 20 is in the closed orientation. The inner surface of the platform 20 may include a heat shield, not shown in the figures, having thermal insulating properties that can maintain structural integrity and prevent other components of the platform 20 from being exposed to high temperatures when the platform 20 is pivoted into the closed position. By way of example, the heat shield 46 may include one or a combination of the following materials; polycarbonate, ABS, PMMA (acrylic), HIPS (high impact polystyrene), noryl (PPO or PPE blended with polystyrene), glass filled nylon, and polysulphone.

Although not shown in detail in the Figures, suitable seals are provided between the various ports and disconnectable parts of the adjustable flow path. For example, co-operating seals may be provided between the housing outlet port 14 and the chamber inlet 31, between the housing inlet port 15 and the chamber outlet 32, between the conduit port 48 and the user conduit 16, between the housing outlet port 14 and the path inlet, and between the housing inlet port and the path outlet. The seals may include suitable sealing structure to facilitate a sealed connected and thus minimise leakage of the gas stream. This reduces noise of the blower 12 being emitted from the apparatus 10 and mitigates losses in the flow rate and pressure of gas stream being delivered to the user. Examples of suitable sealing means include: a flexible pressure seal, inflated sealing ring, and an O-ring within or about the openings of the housing outlet and inlet ports 15 and 14, and/or about the openings of the chamber inlet and outlets 31 and 32.

In one example, the sealed connection may include the chamber inlet 31 and the chamber outlet 32 being received within the housing outlet port 14 and the chamber inlet port 15 respectively. Alternatively, the sealed connection may include the housing outlet port 14 and the housing inlet port 15 being received within the chamber inlet 31 and the chamber outlet 32 respectively. In another example, the sealing connection could be a combination of the two alternatives described in this paragraph.

The user conduit 16 may be non-rotatably or rotatably coupled to the housing conduit port 48. The housing 11 may further include an auxiliary electrical connection (not shown) located adjacent the conduit port, and the user conduit 16 may further include a heating and/or sensing circuit to regulate the temperature of the gases through the user conduit 16 and/or to sense properties of gases within the user conduit 16. The user conduit 16 may have an electrical connector configured to connect to the electrical connection on the housing 11, so that the heating circuit may be powered.

Ideally, the humidification chamber 18 has a double-walled construction. The double-walled construction defines the water tub 33 and an outer chamber 34. The outer chamber 34 overlaps the housing outlet port 14 and the housing inlet port 15. The double-walled structure further improves sound insulation, which further reduces the noise from the blower 12, and thermal insulation of the humidification chamber 18.

In another embodiment, rather than the outer chamber 34 being occupied by gas, it will be appreciated that a sound insulating material may be located in the outer chamber 24. Moreover, it will be appreciated that the double-walled construction of the humidification chamber 18 may be replaced with a single wall structure.

FIG. 2B is a schematic view of a removable humidification chamber 18 that has been separated from the apparatus 10 shown in FIG. 1. As can be seen, the humidification chamber 18 has a water tub 33 with a heater base 40 at the bottom of the water tub 33. To secure the chamber in the operating position, the humidification chamber 18 has: i) a first coupling assembly 41 including a first latching portion 41*a* for co-operating with the second latching portion 41*b* of the housing 11 and; ii) a second coupling assembly 42 including a second latching portion 42*b* for co-operating with the third latching portion 42*a* of the platform 20.

The humidification chamber 18 in FIG. 2B also includes a first passageway 51 extending from a chamber inlet 31 and which opens into a gas chamber 34 for supplying an unhumidified gas stream, and a second passageway 52 extending from the gas chamber 34 to a chamber outlet 32 for discharging a humidified gas stream. The humidification chamber 18 can be used to supply the humidified gas stream back to the housing 11 when the apparatus is being used in the return configuration.

FIG. 4B is a schematic view of a removable humidification chamber 18 that has been separated from the apparatus shown in FIG. 3. As can be seen, the humidification chamber 18 has a water tub 33 with a heater base 40 at the bottom of the water tub 33. To secure the humidification chamber 18 in the operating position, the humidification chamber 18 has: i) a first coupling assembly 41 including a first latching portion 41*a* for co-operating with the second latching portion 41*b* of the housing 11 and; ii) a second coupling assembly 42 including a second latching portion 42*b* for co-operating with the third latching portion 42*a* of the platform 20.

The humidification chamber 18 in FIG. 4B also includes a first passageway 51 extending from a chamber inlet 31 which opens into a gas chamber 34 for supplying an unhumidified gas stream, and a second passageway 52 extending from the gas chamber 34 to a chamber outlet 32 for discharging a humidified gas stream. The humidification chamber 18 can be used to supply the humidified gas stream back to the housing 11 when the apparatus is being used in the return configuration.

FIG. 6B is a schematic view of a removable humidification chamber 18 that has been separated from the apparatus shown in FIG. 5. As can be seen, the humidification chamber 18 has a water tub 33 with a heater base 40 at the bottom of the water tub 33. To secure the humidification chamber 18 in the operating position, the humidification chamber 18 has: i) a first coupling assembly 41 including a first latching portion 41*a* for co-operating with the second latching portion 41*b* of the housing 11 and; ii) a second coupling assembly 42 including a second latching portion 42*b* for co-operating with the third latching portion 42*a* of the platform 20.

The humidification chamber 18 in FIG. 6B also includes a first passageway 51 extending from a chamber inlet 31 which opens into a gas chamber 34 for supplying an unhumidified gas stream, and a second passageway 52 extending from the gas chamber 34 to a chamber conduit port 56 to which the user conduit 16 can be connected. In other words, the humidification chamber 18 is suitable for use in an apparatus 10 in which the apparatus is being used in non-return configuration.

With reference to FIGS. 7 to 12, the apparatus 100 includes a housing 111 having a main body 147 and a platform 120 that is hinged to the housing 111 by hinge mechanism 121 at a lower end of the platform 120, and a blower 112 for generating a gas stream located within the main body 147 of the housing 111. The blower 112 draws ambient air into the blower through an air inlet filter 113. If required, supplemental oxygen can be added to the ambient air to enrich the gas stream with oxygen; the supplemental oxygen can be added at any suitable part of the gas stream, e.g. before the blower, after the blower, after the humidifier, or at the patient interface. The housing 111 has a housing outlet port 114 in the main body 147 that is in communication with an outlet of the blower 112, and a housing inlet port 115 in the main body 147 that is in communication with a user conduit 116 that supplies the gas stream, which will either be a humidified gas stream or a non-humidified gas stream, to a user interface 117. The apparatus 110 also includes a removable humidification chamber 118 containing an amount of water for humidifying the gas stream 119. The apparatus 110 also includes a user display 122, such as an LCD, plasma or other display, and optionally a touch-screen having control buttons.

Figure 7:
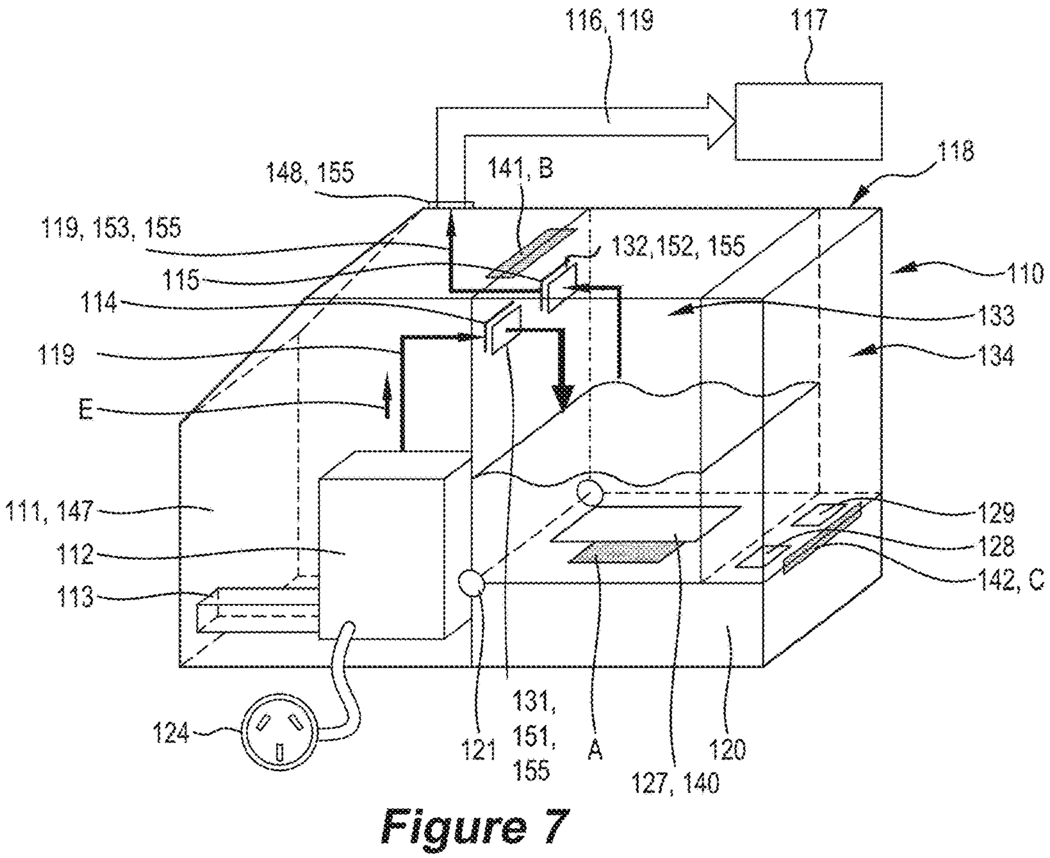
FIG. 7 is a schematic perspective view of the apparatus in a humidifying mode. The apparatus has been illustrated as if partially transparent to show some of the internal components including a blower for generating a gas stream. The arrows indicate the direction of flow of the gas stream along an adjustable flow path arranged in a return configuration that extends from the blower to a removeable humidification chamber, and from the removable humidification chamber to a user conduit. The apparatus also has a platform on which the removable humidification chamber is loaded in an operating position.
Figure 8:
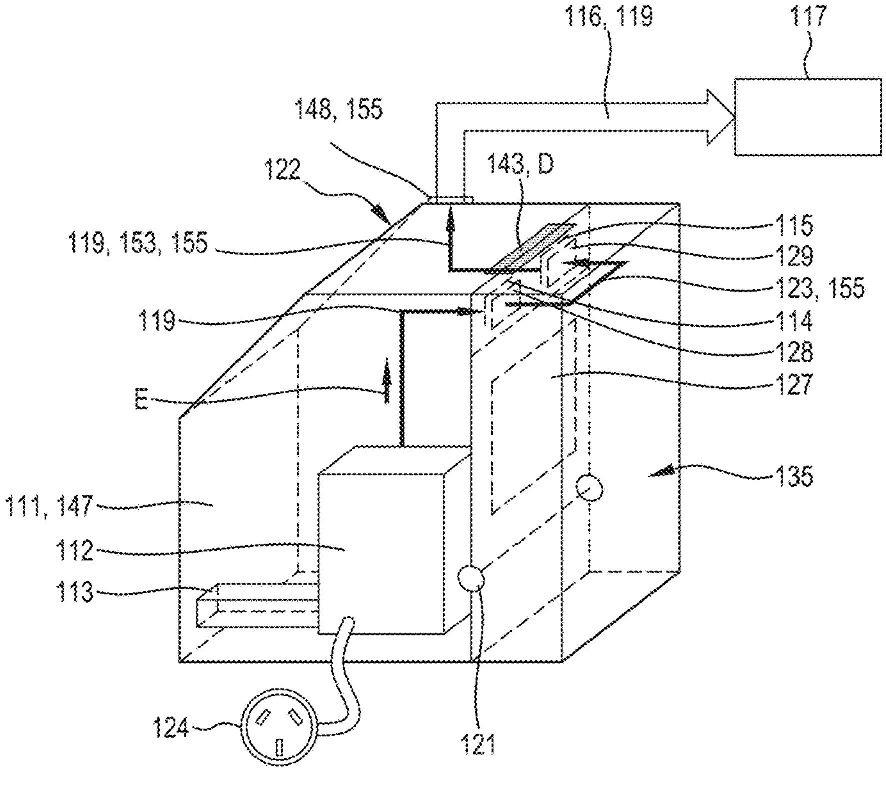
FIG. 8 is a schematic perspective view of the apparatus shown in FIG. 7 in a non-humidifying mode, in which the removable humidification chamber has been removed and the platform pivoted into a closed orientation so as to locate an auxiliary flow path for the gas stream in an active position. The arrow indicates the direction of flow of the gas stream from the blower to the auxiliary flow path, and from the auxiliary flow path to the user via the outlet port of the housing and the conduit.
Figure 9:
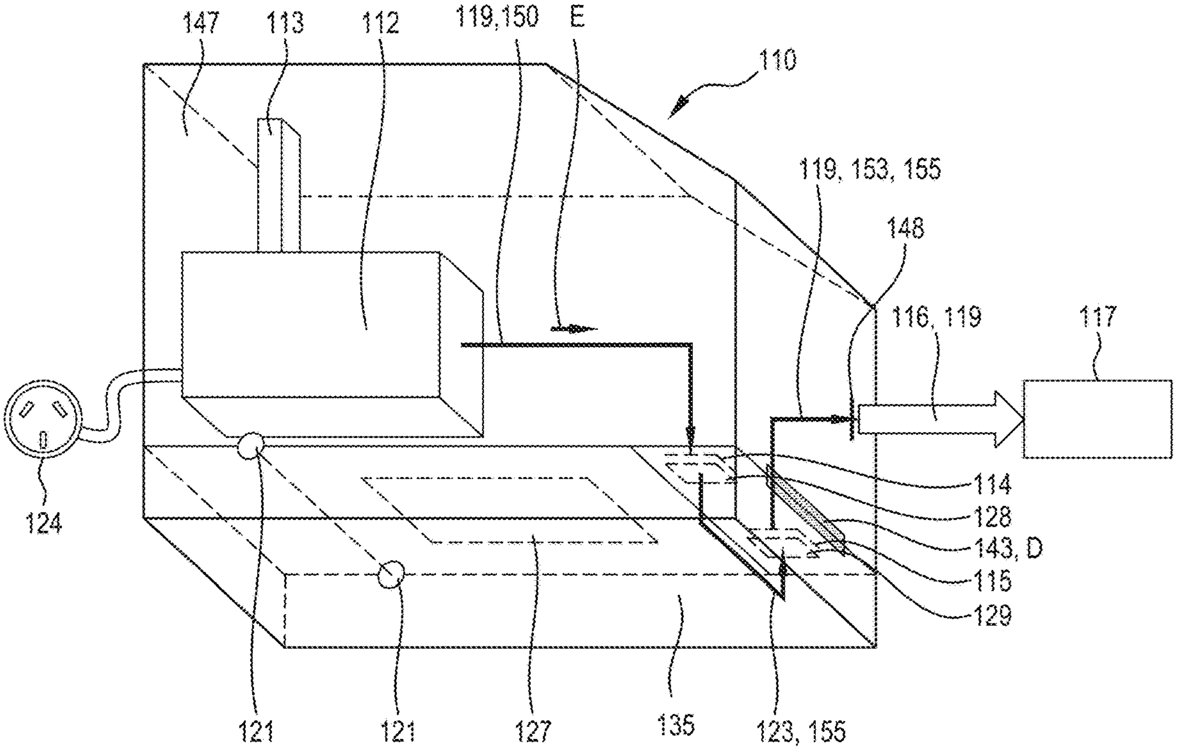
FIG. 9 is a schematic perspective view of the apparatus shown in FIG. 7 in which the apparatus has been laid on the platform.
Figure 11:
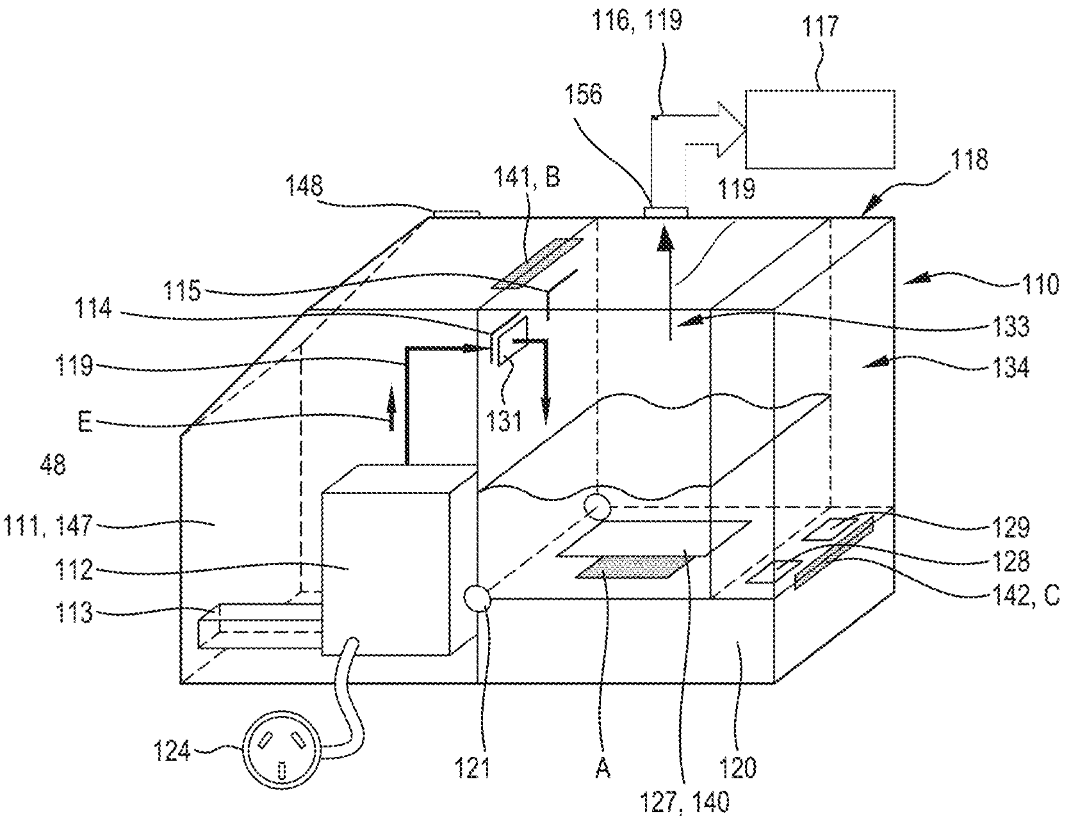
FIG. 11 is a schematic perspective view of the apparatus shown in FIG. 7 in a humidifying mode and in which a user conduit has been connected to a chamber conduit port. The apparatus having an adjustable flow path that is arranged in a non-returned configuration.

The platform 120, which carries an auxiliary flow path 123, can be pivoted into an open orientation, as shown in FIGS. 7 and 11, so that the auxiliary flow path 123 is in an inactive position. The auxiliary flow path 123 is best depicted in FIGS. 8 and 9.

In the humidifying mode, the humidification chamber 118 is loaded or seated on the platform 120 in an operating position, and the auxiliary flow path 123 is in the inactive position. FIGS. 8 and 9 illustrate the apparatus 110 in the non-humidifying mode, in which the humidification chamber 118 is separate from the platform 120 and the platform 120 has been pivoted into a closed orientation so that the auxiliary flow path 123 is active for conveying the gas stream. A benefit of the preferred embodiment is that the apparatus 110 can be switched between the humidifying mode, as shown in FIG. 7, and the non-humidifying mode, as shown in FIGS. 8 and 9, quickly and easily by a user who may have limited hand dexterity. Switching the apparatus 110 between modes can be achieved by fitting or removing the humidification chamber 118 and folding the platform 120 between opened and closed orientations. It is believed that such actions are comparatively intuitive and easy for a user.

The apparatus 110 illustrated FIGS. 7 to 12 also has an adjustable flow path 155 that can change configuration. Specifically, the adjustable flow path 155 of the apparatus 110 in FIGS. 7 to 9 has a return configuration in both the humidifying mode and the non-humidifying mode. As mentioned above, when the apparatus 100 is in the non-humidifying mode, the auxiliary flow path section 123 is located in an active position and characterizes the return configuration by the gas stream 119 passing though the auxiliary flow path section 123 back to the main body 147 of the housing 111.

FIG. 11 illustrates the apparatus 110 having an adjustable flow path 155 in a non-return configuration while the apparatus 110 is in the humidifying mode. In this configuration, the user conduit 116 is connected to the chamber conduit port 156. Although not necessary for using the apparatus 110 in the non-return configuration, the housing may also include an inlet port 115, a housing conduit port 148, and a removeable section 153, the later not being shown in FIG. 11. If there was a need to operate the apparatus 110 in FIG. 11 in a return configuration in the humidification mode, the humidification chamber 118 in FIG. 11 could be replaced with the chamber 118 shown in FIG. 10 which has a chamber outlet 132 instead of the chamber conduit port 156.

In the case of FIGS. 7 to 9, 12 and 13, the adjustable flow path 155 comprises a fixed section 150 of ducting extending from, and includes, an outlet of the blower 112 to the housing outlet port 114. The direction of flow of the gas stream 119 in the ducting is indicated by arrow E. The humidification chamber 118 has a chamber inlet 131 that connects to the housing outlet port 114, and the adjustable flow path 155 includes: a first passageway 151 for the gas stream extending from the chamber inlet 131 to a water tub 133, and a second passageway 152 for conveying the gas stream 119 extending from the water tub 133 to a chamber outlet 132. When the apparatus 110 is in the non-humidifying mode, the humidification chamber 118 is removed from the main body 147 and the first and second passageways 151 and 152 do not form part of the adjustable flow path 155. When the apparatus 110 is in the humidifying mode, the humidification chamber 118 is loaded onto the main body 147 of the apparatus 110, and the first and second passageways 151 and 152 form part of the adjustable flow path 155.

The adjustable flow path 155 of the embodiments in FIGS. 7, 8, 9 and 11 further include a removable section 153 that extends from, and includes, the housing inlet port 115 to a housing conduit port 148 for connecting to a user conduit 116 that conveys the gas stream 119 to a user interface 117. The removable section 153 therefore conveys the gas stream when humidified, and the removable section 153 can be replaced and/or cleaned in accordance with a suitable hygiene regime.

In addition, the adjustable flow path 155 of the embodiment illustrated in FIGS. 7 to 9 includes an auxiliary flow path section 123 that has a passageway including a path inlet 128 and a path outlet 129 that forms part of, or is attached to, the platform 120. The auxiliary flow path 123 has an inactive position in which the auxiliary flow path section 123 does not form part of the adjustable flow path 155 and corresponds to when the platform 120 is not in the closed orientation, i.e., an opened orientation. For example, when the platform 120 is pivoted fully opened, the humidification chamber 18 can be loaded onto the housing 11 as shown in FIG. 7.

In the case of the embodiment illustrated in FIGS. 8 and 9, the auxiliary flow path section 123 also has an active position which forms part of the adjustable flow path 155 when the platform 120 is pivoted into the closed orientation and the path inlet 128 connects to the housing outlet port 114 and the path outlet connects to the housing inlet port 115. The auxiliary flow path section 123 is therefore located in the active position only when the apparatus 110 is being operated in the non-humidifying mode.

As shown in FIG. 11, when the apparatus 110 is in the non-return configuration, the gas stream 119 is conveyed straight into the user conduit 116 via the chamber conduit port 156. In this instance the removeable section 153 and the housing conduit port 148 can be removed or omitted from the apparatus 110.

As can be seen in FIG. 7, the housing 111 is connected to a power source via an electrical coupling 124 which powers the blower 112 and other components. If required, the apparatus 110 can include a rechargeable battery for powering the apparatus 110 when mains electricity is not available.

The blower 112 has an outlet which is flow connected to the housing outlet port 114 of the housing 111 via a suitable ducting. The direction of flow of the gas stream in the ducting is indicated by arrow E in FIGS. 7 to 9.

The housing inlet port 115 is flow connected to a housing conduit port 148 via a gases return. The user conduit 116, may be coupled to, and receive gases from, the housing conduit port 148, and convey the gas stream to a user interface 117. The user conduit 116 may be non-rotatably or rotatably coupled to the housing outlet 114. The housing 111 may further include an auxiliary electrical connection (not shown) located adjacent the housing conduit port 148, and the user conduit 116 may further include a heating circuit to regulate the temperature of the gases through the user conduit 116. The user conduit 116 may have an electrical connector configured to connect to the electrical connection on the housing 111, so that the heating circuit may be powered.

Figure 12:
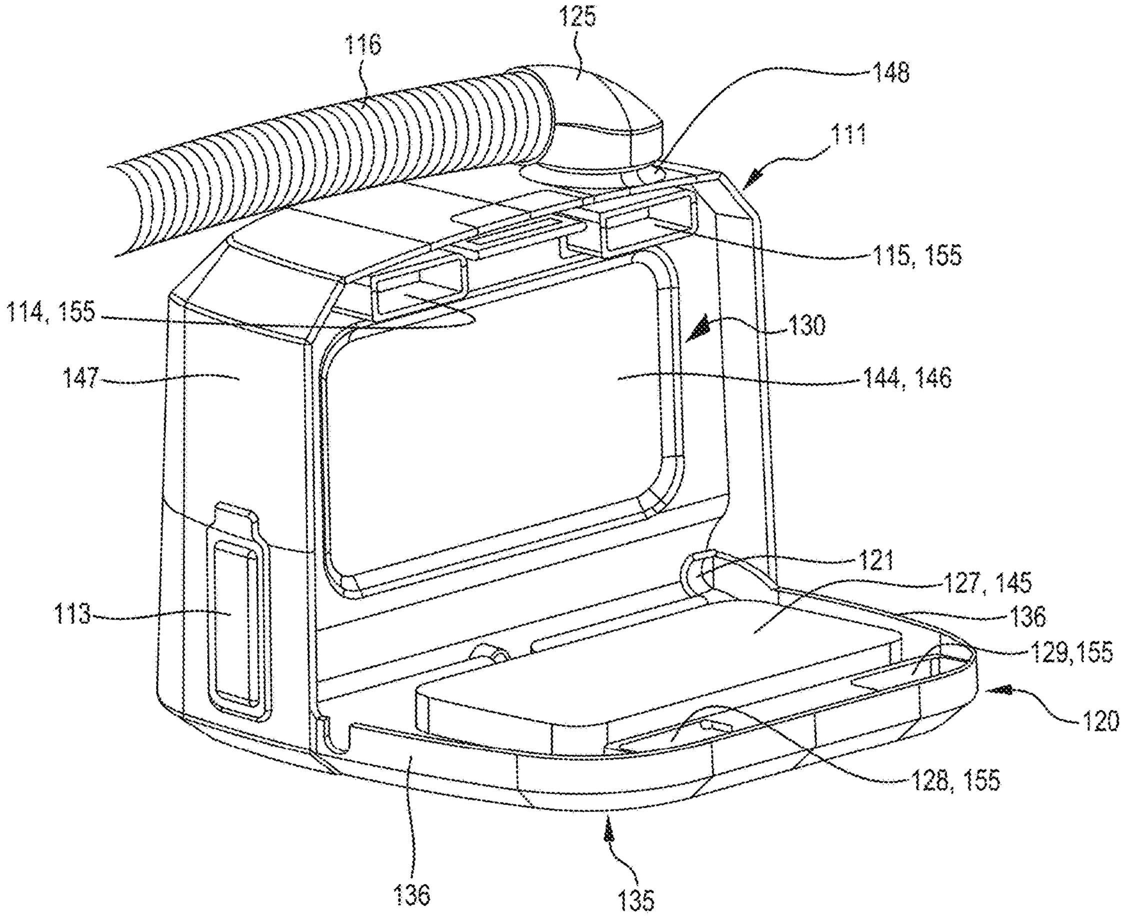
FIG. 12 is a perspective view of the apparatus shown in FIG. 7 without the humidification chamber and illustrates the components of the platform and components of the housing including an inlet port and an outlet port. The apparatus shown in FIG. 12 shows the apparatus without the chamber, that is, the chamber is separate, and the auxiliary flow path is in an inactive position.
Figure 13:
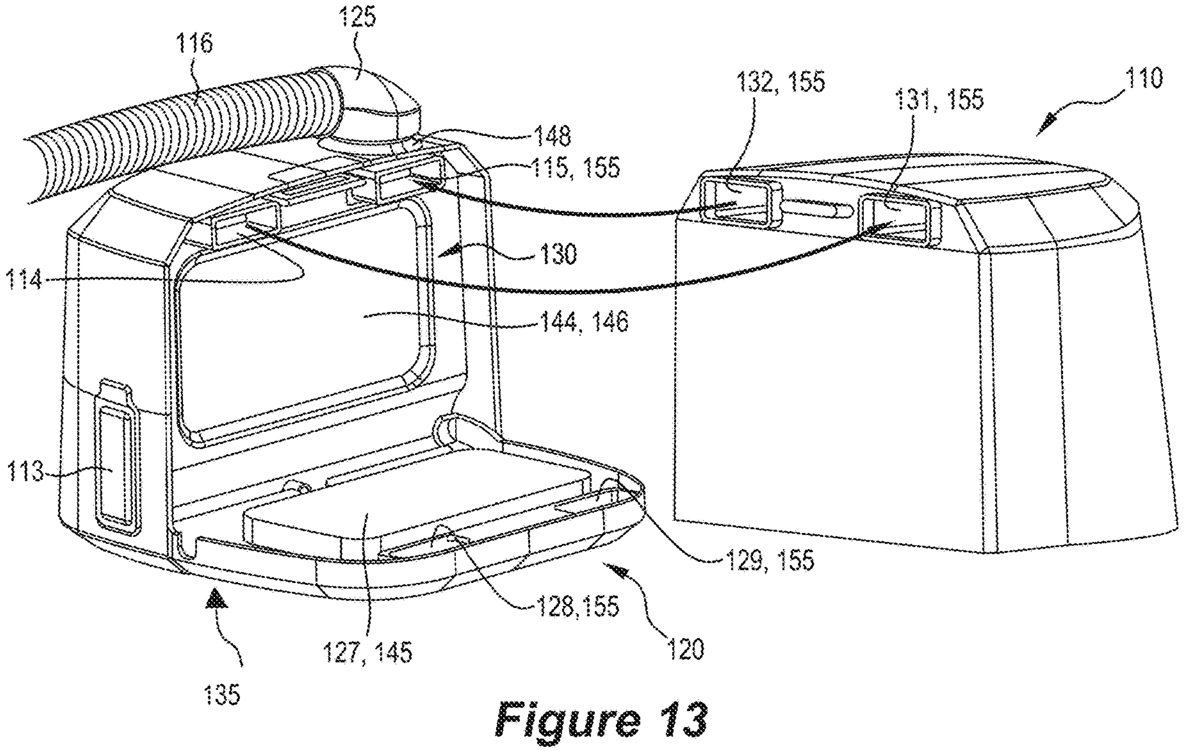
FIG. 13 is a perspective view of the apparatus shown in FIG. 7 in an exploded view with the humidification chamber spaced from the housing of the apparatus and the arrows indicating the alignment of the inlet port and the outlet port of the housing with the inlet and outlet of the chamber for using the apparatus in the humidifying mode.

In the humidifying mode, the platform 120 is pivoted into the opened orientation, as shown in FIGS. 7, 11 and 12. FIGS. 11 and 12 illustrate an inner surface 145 of the platform 120, which is positioned adjacent an internal side wall 130 of the housing 111 when the platform 120 is in the closed position. The inner surface 145 of the platform 120 has a heater assembly including a heater plate 127, and a path inlet 128 and path outlet 129 of the auxiliary flow path 123. FIGS. 11 and 12 also illustrate an internal side wall 130 of the housing 111. The internal side wall 130 includes a recess 144 that at least partly receives the heater plate 127 when the platform 120 is in the closed orientation. The internal side wall 130 may also include a heat shield 146 having thermal insulating properties that can maintain structural integrity and prevent other components of the housing from being exposed to high temperatures when the platform 120 is pivoted into the closed position. By way of example, the heat shield 146 may include one or a combination of the following materials; polycarbonate, ABS, PMMA (acrylic), HIPS (high impact polystyrene), noryl (PPO or PPE blended with polystyrene), glass filled nylon, and polysulphone.

The internal side wall 130 also includes the housing outlet port 114 and the housing inlet port 115.

The humidification chamber 118 also includes a chamber inlet 131 that connects to the housing outlet port 114 and a chamber outlet 132 that connects to the housing inlet port 115. The arrows in FIG. 12 indicate the alignment of the chamber inlet 131 to the housing outlet port 114, and the alignment of the chamber outlet 132 to housing inlet port 115. As can best be seen in FIG. 7, the chamber inlet 131 and the chamber outlet 132 are ideally located above the maximum water level in the humidification chamber 118.

Although not shown in detail in the Figures, the housing outlet port 114 which co-operates with the chamber inlet 131 and the path inlet 128, and the housing inlet port 115 which co-operates with the chamber outlet 132 and the path outlet 129, may include suitable sealing means to facilitate a sealed connected therebetween, and thus minimise leakage of the gas stream. This reduces noise of the blower 112 being emitted from the apparatus 110 and mitigates losses in the flow rate and pressure of gas stream being delivered to the user. Examples of suitable sealing means include: a flexible pressure seal, inflated sealing ring, and an O-ring within or about the openings of the housing outlet and inlet ports 115 and 114, and/or about the openings of the chamber inlet and outlets 131 and 132.

In one example, the sealed connection may include the chamber inlet 131 and the chamber outlet 132 being received within the housing outlet port 114 and the chamber inlet port 115 respectively. Alternatively, the sealed connection may include the housing outlet port 114 and the housing inlet port 115 being received within the chamber inlet 131 and the chamber outlet 132 respectively. In other example, the sealing connection could be a combination of the two alternatives described in this paragraph.

Figure 10:
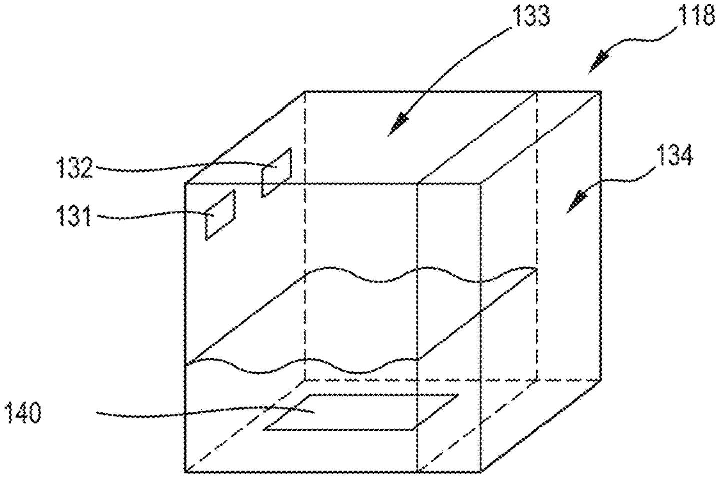
FIG. 10 is a schematic perspective view of the removeable humidification chamber of the apparatus in FIG. 7 that has been separated from the apparatus.

As can be best seen in FIG. 10, the humidification chamber 118 has a double-walled construction. The double-walled construction defines an inner water tub 133 and an outer chamber 134. The outer chamber 134 overlaps the path inlet 128 and path outlet 129 of the auxiliary flow path 123, and can form a gas chamber. The outer chamber 134 extends about at least one panel of the water tub 133. However, it will be appreciated that the outer chamber 134 may extend about all side panels defining of the water tub 133. The double-walled structure further improves sound insulation, which further reduces the noise from the blower 112, and thermal insulation of the humidification chamber 118. The humidification chamber 118 also has a heater base 140 at a bottom wall of the water tub 133, a chamber inlet 131 for supplying an unhumidified gas stream into a gas compartment of the water tub 133, and a chamber outlet 132 for supplying an humified gas stream back to the housing 111 when the apparatus is being used in a return configuration.

In another embodiment, rather than the outer chamber 134 been occupied by gas, it will be appreciated that a sound insulating material may be located in the outer chamber 124. Moreover, it will be appreciated that the double-walled construction of the humidification chamber 118 may be replaced with a single wall structure.

The platform 120 has an outer surface 135 which when in the opened orientation in the humidifying mode faces downwardly, a peripheral sidewall 136 extending upwardly from the base 135. The hinge mechanism 121 which pivotally connects the platform 120 to the housing 111 may be any suitable hinge mechanism.

Examples of a suitable hinge mechanism include a concealed hinge, a continuous hinge, a knife hinge, or a spring-loaded hinge. Ideally, the hinge mechanism has a controller that controls the rate at which the platform 120 moves from the closed orientation to the opened orientation. Although not shown in the Figures, the controller may include one or more of: a torque spring, gas struts, coiled springs, or hydraulic mechanisms.

Although not shown in the Figures, a latch may releasably secure the platform 120 in the opened orientation. The latch can be released to allow the platform 120 to be moved from the opened orientation to the closed orientation.

The inner surface of the platform 120 has a heater plate 127 centrally located of the platform 120, and the auxiliary flow path 123 located toward an outer end of the platform 120, which becomes the upper end when viewing the apparatus 111 in the orientation shown in FIG. 8.

The heater plate 127 includes a planar surface that is heated using electrical power. As can be seen in FIGS. 11 and 12, the heater plate 127 has a sidewall structure which is extends upward from the platform 120. The heater plate 127 may have any suitable structure, and may include a biasing device (not illustrated in the Figures) that urges the heater 137 away from the base 135 of the platform 120, such that when the humidification chamber 118 is loaded onto the platform 120, the heater plate 127 presses against the humidification chamber 118 to enhance thermal engagement therebetween.

The apparatus 110 may also include one or more locators which provide alignment of the inlet port 115 of the housing 111 with the chamber inlet 131 of the humidification chamber 118 and the outlet port 115 with the chamber outlet 132 when the apparatus is in the humidifying mode. For example, an outer wall 138 of the humidification chamber 118 may be seated on the peripheral sidewall 136 of the platform 120. The peripheral sidewall 136 of the platform 120 may include a channel formation in which the outer wall 138 of the humidification chamber 118 is received. Alternatively, the peripheral side wall may be at least partially received in a channel formation in the outer wall 138 of the humidification chamber 118.

Another example of a locator may be an apron, represented by box A in FIG. 7, that extends downwardly from the bottom wall 139 of the humidification chamber 118, and the apron fits about the sidewall of the heater plate 127. The apron may be sized so that the heater plate 127 is frictionally fitted within the apron and thermally engages a thermally conductive heater base 140 of the humidification chamber 118. The heater base 140 may be constructed from any suitable thermally conductive material. In a preferred form the heater base is constructed from aluminium. The heater base may be a pressed aluminium sheet.

In the humidifying mode, the heater base 140 of the humidification chamber 118 overlays and thermally engages the heater plate 127 to heat and evaporate water in the chamber 118.

The humidification chamber 118 may be coupled to the housing 111 in the humidifying mode by a first coupling assembly 141 which is depicted box B in FIG. 7. The first coupling assembly releasably connects a top edge of the humidification chamber 118 to an upper section of the housing 111, when seen in the orientation in FIG. 7. The first coupling assembly 141 includes: a first latching portion on an upper edge of the humidification chamber 118 which engages a second latching portion on an upper section of the housing 111.

Similarly, the humidification chamber 118 may also be coupled to the platform 120 in the humidifying mode by a second coupling assembly 142, which is depicted by box C in FIG. 7. The second coupling assembly 142 releasably connects an outer section of the platform 120 to a lower outer section of the humidification chamber 118. The second coupling assembly 142 includes a third latching portion on an outer edge of the platform 120 and/or on the auxiliary flow path which engages a fourth latching portion on an outer lower edge of the humidification chamber 118.

A third coupling assembly 143 may also couple the outer section of the platform 120 to the housing 111 when the platform 120 is in the closed orientation. The third coupling assembly 143 is depicted by box D in FIGS. 8 and 9, and includes the third latching portion engaging the second latching portion.

Examples of different mechanisms suitable for coupling and locating the humidification chamber to the housing, coupling and locating the platform to the humidification chamber, and coupling the platform to the housing when the platform is in the closed orientation, include: a sliding connector, a screw connector, a bayonet connector, a magnet connector, a push-latch connector, or a male-female interference fit connector.

The auxiliary flow path 123 is arranged at the outer end of the platform 120. As can best be seen in FIGS. 11 and 12, the path inlet 128 and the path outlet 129 of the auxiliary flow path 123 are releasably connected to the housing inlet port 115 and the housing outlet port 115. In the humidifying mode, the auxiliary flow path 123 is located in the inactive position and the humidification chamber 118 is placed in the operating position as shown in FIG. 7. Similarly, the platform 120 may be pivoted into the opened orientation and the humidification chamber 118 may either be in the process of being removed from the apparatus 110 or fitted to the apparatus 110. In any event, when the platform 120 is pivoted into the opened orientation, and the humidification chamber 118 is not fitted to the apparatus 110, and thus the apparatus 110 is not operable in either the humidifying mode or the non-humidifying mode.

In the non-humidifying mode, the auxiliary flow path 123 must be located in the active position which, in the preferred embodiment, is provided by the platform 120 being pivoted into the closed position. Specifically, in the closed position the path inlet 128 communicates with the housing outlet port 114, and the path outlet 129 communicates with the housing inlet port 115.

FIG. 9 illustrates the apparatus 110 with the platform 120 located in the closed orientation, and the apparatus 110 lying horizontally on the outer surface 135 of the platform 120. By laying the housing 111 of the apparatus 110 horizontally, the apparatus 110 is located in a more stable orientation in the absence of the humidification chamber 118.

To enable the apparatus 110 to be used in both the upright orientation, as shown in FIGS. 7 and 8, and in a horizontal orientation, as shown in FIG. 9, the user display 122 may have direction sensors to enable the output of the display 122 to change orientation to accommodate the orientation of the apparatus 110.

FIG. 14 is a table of method steps of operating an apparatus to provide respiratory assistance to a user, in which the method includes operating the apparatus in a humidifying mode and a non-humidifying mode. The method steps can be summarised as set out below, however, the order of the steps below does not necessarily reflect the order in which the steps are undertaken.

i) Providing a housing having a gas stream outlet port and a gas stream inlet port.

ii) Operating a blower that generates a gas stream and conveying the gas stream through the gas stream inlet port.

iii) Moving an auxiliary flow path into an inactive position in which the auxiliary flow path is remote from the inlet port and the outlet port, in the humidifying mode. For example, moving the auxiliary flow path may include pivoting a platform on which the auxiliary flow path is mounted between a closed orientation to an opened orientation. The platform is in the open orientation in FIGS. 7 ad 8.

iv) Locating a humidification chamber in an operating position in which an inlet of the humidification chamber communicates with the inlet port of the housing and in which an outlet of the chamber communicates with the outlet port of the housing, thereby allowing the gas stream to be conveyed through the chamber for humidification of the gas stream in the humidifying mode. For example, the locating the humidification in the operating position may include locating the platform in the opened orientation and loading the humidification onto the platform and operating coupling assemblies that retain the humidification chamber in the operation position.

v) Conveying the humidified gas stream through the outlet port of the housing and to a user via a swivel coupling and conduit.

vi) Removing the humidification chamber from the operating position, and moving the platform from the opened orientation to a closed orientation, as shown for example in FIGS. 8 and 9, which locates the auxiliary flow path in an active position where the auxiliary flow path communicates with the outlet port and the inlet port of the housing in the non-humidifying mode.

vii) Conveying the gas stream from the inlet port of the housing in the non-humidifying mode to a user via a housing outlet and conduit.

Those skilled in the art of the present invention will appreciate that many variations and modifications may be made to the preferred embodiment without departing from the spirit and scope of the present invention.

For example, rather than the platform being pivotally attached to the housing as shown in the Figures, the platform may be detached from the housing when changing the orientation of the platform. Once detached from the housing, the platform may be reattached to the housing in either the opened orientation to facilitate use of the apparatus in the humidifying mode, or in the closed orientation to facilitate use of the apparatus in the non-humidifying mode as required. The platform may be attached to the housing in either the humidifying mode or the non-humidifying mode using any suitable connector(s), including a latch connector, a magnetic connector, a screw connector, a bayonet connector, a male-female interference fit connector and so forth. The housing and the platform may also include suitable electrical couplings that can be decoupled when the platform is detached from the housing and, similarly, reconnected for powering the heater plate of the platform when the platform is reattached to the housing in either the opened orientation or the closed orientation. The electrical couplings may include a pin and socket connector.

Although not shown in detail in Figures, the humidification chamber may include a removable lid across the entire face of the humidification chamber or only part thereof. When the humidification chamber has been detached from the housing, the lid can be opened or detached from the humidification chamber to facilitate refilling and/or cleaning of the humidification chamber as required.

Although not illustrated in detail, the user interface, depicted by reference numerals 17 and 117 may comprise any suitable device for delivering the gas stream to the airways of a patient, including for example: a nasal mask, an oro-nasal mask, an oral mask, a full face mask, a nasal cannula and nasal pillows.

Throughout this specification the terms "humidification chamber" and "chamber" are used interchangeably, and the terms "humidification apparatus" and "apparatus" are also used interchangeably.

In the claims which follow, and in the preceding description, except where the context requires otherwise due to express language or necessary implication, the word "comprise" and variations such as "comprises" or "comprising" are used in an inclusive sense, i.e. to specify the presence of the stated features but not to preclude the presence or addition of further features in various embodiments of the apparatus and method as disclosed herein.

In the foregoing description of preferred embodiments, specific terminology has been resorted to for the sake of clarity. However, the invention is not intended to be limited to the specific terms so selected, and it is to be understood that each specific term includes all technical equivalents which operate in a similar manner to accomplish a similar technical purpose. Terms such as "front" and "rear", "inner" and "outer", "above", "below", "upper" and "lower" and the like are used as words of convenience to provide reference points and are not to be construed as limiting terms. The terms "vertical" and "horizontal" when used in reference to the humidification apparatus throughout the specification, including the claims, refer to orientations relative to the normal operating orientation.

Furthermore, invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, for example, aspects of one embodiment may be combined with aspects of another embodiment to realize yet other embodiments. Further, each independent feature or component of any given assembly may constitute an additional embodiment.

For instance, although not shown in Figures, the humidification chamber may also have external fixtures and internal fixtures such as noise reduction structures, spill-blocks to prevent spillage of water from the humidification chamber either upstream or downstream in the direction of flow of the gas stream to avoid contact with the powered devices, and baffles that prevent gas flow short circuiting through the humidification chamber. The specification of International patent publication WO2005/018724, which is hereby incorporated into this specification by express reference, includes examples of a number of these fixtures that could be added the humidification chamber described herein.

Statements

1. An apparatus for providing respiratory assistance to a user via a user conduit, the apparatus being operable in a humidifying mode and a non-humidifying mode, the apparatus includes:

a blower for generating a gas stream;

an adjustable flow path for the gas stream to which the user conduit can be connected;

a housing having at least part of the adjustable flow path that extends from the blower to a housing outlet port;

a humidification chamber having a chamber inlet and the humidification chamber being movable and can be located in:

i) an operating position in which the chamber inlet communicates with the housing outlet port to convey the gas stream through the humidification chamber, the humidification chamber forming part of the adjustable flow path which operates the apparatus in the humidifying mode, and ii) a non-operating position in which the humidification chamber is separate from the housing, and does not form part of the adjustable flow path which operates the apparatus in the non-humidifying mode.

2. The apparatus according to statement 1, wherein the adjustable flow path has a conduit port that includes either one or a combination of a chamber conduit port or a housing conduit port to which the user conduit can be connected.

3. The apparatus according to any one of the preceding statements, wherein the chamber conduit port is located on the humidification chamber for the gas stream to exit directly from the humidification chamber, and the user conduit is connected to the chamber conduit port when the apparatus is in the humidifying mode.

4. The apparatus according to statement 2, wherein the housing conduit port is located on the housing and the user conduit is connected to the housing conduit port when the apparatus is in the humidifying mode or the non-humidifying mode.

5. The apparatus according to any one of the preceding statements, wherein the adjustable flow path has a return configuration when the apparatus is in the humidifying mode, in which the flow path extends from the housing to the humidification chamber, and returns to the housing.

6. The apparatus according to any one of the preceding statements, wherein the adjustable flow path has a non-return configuration when the apparatus is in the humidifying mode, in which the flow path exits the humidification chamber without returning to the housing.

7. The apparatus according to any one of the preceding statements, wherein the housing has a housing inlet port and the humidification chamber has a chamber outlet, and when the humidification chamber is in the operating position the adjustable flow path has a return configuration that extends from the housing outlet port to the humidification chamber via the chamber inlet, and returns to the housing inlet port via the chamber outlet and the housing inlet port.

8. The apparatus according to statement 7, wherein the adjustable flow path has a removable section extending from the housing inlet port to the housing conduit port, in which the removable section is detachable from the housing for disinfecting or cleaning purposes.

9. The apparatus according to any one of statements 7 or 8, wherein the apparatus has an auxiliary flow path section that can be located in an active position when the apparatus is in the non-humidifying mode, and in which the auxiliary flow path section communicates with the housing outlet port and the housing inlet port to convey the gas stream therebetween.

10. The apparatus according to statement 9, wherein the auxiliary flow path is pivotally connected to the housing and can pivot between the active position and an inactive position.

11. The apparatus according to statements 9 or 10, wherein the auxiliary flow path has a path inlet and a path outlet, and is in the active position when the apparatus is in the non-humidifying mode, and the path inlet and the path outlet are connected with the housing inlet port and housing outlet port respectively.

12. The apparatus according to any one of statements 9 to 11, wherein the auxiliary flow path can move into the inactive position when the apparatus is in the humidifying mode, such that the path inlet and the path outlet are disconnected from the housing inlet port and the housing outlet port respectively.

13. The apparatus according to any one of statements 9 to 12, wherein the humidification chamber and the auxiliary flow path section are in flow communication with the housing inlet port and the housing outlet port alternatively.

14. The apparatus according to any one of the preceding statements, wherein the apparatus has a powered device including a heater assembly for heating the water in the humidification chamber.

15. The apparatus according to statements 14, wherein the powered device engages the humidification chamber to heat the water, in which the engagement between the powered device and the humidification chamber includes any one or a combination of thermal engagement, electrical power engagement, and/or an inductive power engagement.

16. The apparatus according to any one of statements 14 or 15, wherein the heater assembly is arranged on an outer face of the main body of the housing to facilitate thermal engagement between the heater assembly and the humidification chamber when the apparatus is in the humidifying mode.

17. The apparatus according to statement 16, wherein the heater assembly may have a heater plate that heats and thermally engages a thermally conductive heater base of the humidification chamber, and in which the heater plate is arranged in a non-movable position on the main body of the housing or in a fixed position.

18. The apparatus according to any one of statements 14 to 17, wherein the powered device includes a heating element arranged in the humidification chamber and an electrical coupling for electrically connecting the heating element to a co-operating electrical coupling of the housing for powering the heating element.

19. The apparatus according to any one of statements 14 to 18, wherein the powered device includes an induction generator in the main body, and a co-operating heater base of the humidification chamber that heats on exposure to energy from the induction generator for heating the water in the humidification chamber.

20. The apparatus according to any one of the preceding statements, wherein the housing has a main body and a platform that is moveable relative to the main body and the blower is housed in the main body.

21. The apparatus according to statement 20 when appended to 17, wherein the heater assembly is moveable relative to the main body which allows the heater plate to be engaged by the humidification chamber when the humidification chamber is located in the operating position.

22. The apparatus according to statement 21, wherein the heater assembly is mounted to an inner surface of the platform and on which the humidification chamber can be seated.

23. The apparatus according to statement 20 when appended to any one of statements 9 to 12, wherein the auxiliary flow path section is on the platform, the path inlet and the path outlet are supported on or form part of the platform, and the platform is moveable relative to the housing.

24. The apparatus according to any one of statements 20 to 23, wherein the humidification chamber is separate from the housing when the apparatus is in the non-humidifying mode which allows the platform to be moved toward the housing to locate the auxiliary flow path section in the active position.

25. The apparatus according to any one of statements 20 to 24, wherein when the auxiliary flow path section is in the inactive position, the humidification chamber can be loaded onto the housing so that so that the chamber inlet and the chamber outlet communicate with the housing inlet port and the housing outlet port respectively.

26. The apparatus according to any one of statements 20 to 25, wherein the platform is pivotally connected to the housing and moves between opened and closed orientations.

27. The apparatus according to statement 26, wherein when the platform is pivoted into a closed orientation, the act of closing the platform moves the auxiliary flow path section to the active position.

28. The apparatus according to statement 26 or 27, wherein the platform can be pivoted into an opened orientation in which the act of opening the platform moves the auxiliary flow path section into the inactive position, and when in the open orientation, the humidification chamber can be loaded onto the housing, allowing the apparatus to be operated in a humidifying mode.

29. The apparatus according to any one of statements 20 to 28, wherein the housing has user controls that a user can use to operate the apparatus, in which the user controls include a display screen located on the platform.

30. The apparatus according to any one of statements 20 to 29, wherein the user controls can be observed by a user when the platform is located in both the opened and closed orientations.

31. The apparatus according to any one of statements 20 to 30, wherein the platform is oriented parallel to the housing in the closed orientation, and the platform is oriented laterally to the main body of the housing in the opened orientation.

32. The apparatus according to any one of statements 20 to 31, wherein the main body of the housing has a base on which the apparatus can be seated when the apparatus is in the humidifying mode and the non-humidifying mode, the main body of the housing having the same orientation in both the humidifying mode and the non-humidifying mode.

33. The apparatus according to any one of statements 20 to 32, wherein the apparatus has a coupling assembly that releasably couples together the main body of the housing and the humidification chamber when the apparatus is in the humidifying mode.

34. The apparatus according to statement 33, wherein the coupling assembly releasably couples together the housing and the platform in the active position when the apparatus is in the non-humidifying mode.

35. The apparatus according to any one of statements 33 or 34, wherein the coupling assembly releasably couples together the housing and the auxiliary flow path when the apparatus is in the non-humidifying mode.

36. The apparatus according to any one of statements 33 to 35, wherein the coupling assembly releasably couples together the humidification chamber and the platform when the apparatus is in the humidifying mode, that is, with the platform in the opened orientation.

37. The apparatus according to any one of statements 20 to 36, wherein the coupling assembly includes: a first latching portion on the body of the humidification chamber and a co-operating second latching portion on the main body of the housing that can releasably engage the first latching portion in the humidifying mode.

38. The apparatus according to statement 37, wherein the coupling assembly includes a third latching portion on the platform and/or the auxiliary flow path that can releasably engage the second latching portion in the non-humidifying mode.

39. The apparatus according to statement 37, wherein the coupling assembly includes a fourth latching portion on the body of the humidification chamber that can be releasably engage the third latching portion on the platform.

40. The apparatus according to any one of statements 20 to 36, wherein the coupling assembly has a locking mechanism for securing the platform at multiple angles of orientation to the main body when in the opened orientation.

41. The apparatus according to any one of statements 33 to 40, wherein the coupling assembly may include a first formation on a body of the humidification chamber, and a second formation on the main body of the housing, and the first and second formations inter-fit when the humidification chamber is located in the operating position to assist in aligning the chamber inlet and the chamber outlet with the housing outlet port and the housing inlet port respectively.

REFERENCE NUMERAL TABLE

| | |
|---|---|
| apparatus | 10, 110 |
| housing | 11, 111 |
| blower | 12, 112 |
| air inlet filter | 13, 113 |
| housing outlet port | 14, 114 |
| housing inlet port | 15, 115 |
| user conduit | 16, 116 |
| user interface | 17, 117 |
| humidification chamber | 18, 118 |
| gas stream | 19, 119 |
| platform | 20, 120 |
| hinge mechanism | 21, 121 |
| user display | 22, 122 |
| auxiliary flow path section | 23, 123 |
| electrical coupling | 24, 124 |
| heater plate | 27, 127 |
| path inlet | 28, 128 |
| path outlet | 29, 129 |
| internal side wall | 130 |
| chamber inlet | 31, 131 |
| chamber outlet | 32, 132 |
| water tub | 33, 133 |

-continued

| | |
|---|---|
| gas chamber | 34, 134 |
| outer surface (of the platform) | 135 |
| peripheral side wall | 136 |
| outer wall (of the humidification chamber) | 138 |
| bottom wall (of the humidification chamber) | 139 |
| heater base | 40, 140 |
| first coupling assembly | 41, 141 |
| first latch portion | 41a |
| second latch portion | 41b |
| second coupling assembly | 42, 142 |
| third latch portion | 42a |
| fourth latch portion | 42b |
| third coupling assembly | 43, 143 |
| recess | 144 |
| inner surface (of the platform) | 145 |
| main body (of the housing) | 47, 147 |
| housing conduit port | 48, 148 |
| fixed section | 50, 150 |
| first passageway | 51, 151 |
| second passageway | 52, 152 |
| removable section | 53, 153 |
| base | 54 |
| adjustable flow path | 55, 155 |
| chamber conduit port | 56, 156 |

The invention claimed is:

1. An apparatus for providing respiratory assistance to a user via a user conduit, the apparatus being operable in a humidifying mode in which a humidification chamber is located in an operating position on the apparatus and a non-humidification mode, wherein the apparatus comprises:

a blower for generating a gas stream;

a housing having a housing outlet port that is in communication with the blower and a housing inlet port, the housing comprising a main body and a platform that is pivotable relative to the main body, the platform being able to be pivoted into a closed orientation in the non-humidification mode and an opened orientation in the humidifying mode; and a heating assembly that is moveable relative to a part of the housing, and in the humidifying mode, the heating assembly is configured to be located in an operating position in which the humidification chamber is configured to be engaged by the heating assembly and, in the non-humidification mode, the heating assembly is configured to be located in a stowed position in which the humidification chamber is unable to be loaded on the heating element assembly.

2. The apparatus according to claim 1, wherein the housing inlet port is configured to communicate with the user conduit.

3. The apparatus according to claim 1, wherein the apparatus comprises the humidification chamber for containing water, the humidification chamber comprising a chamber inlet that communicates with the housing outlet port and a chamber outlet that communicates with the housing inlet port to convey the gas stream through the humidification chamber.

4. The apparatus according to claim 1, wherein the heating assembly receives power for heating water in the humidification chamber to increase humidification of the gas stream.

5. The apparatus according to claim 1, wherein the heating assembly engages the humidification chamber to heat water, in which engagement between the heating assembly and the humidification chamber is configured to be any one or a combination of thermal engagement, electrical power engagement, and/or an inductive power engagement.

6. The apparatus according to claim 1, wherein the heating assembly is arranged on an outer face of the main body to facilitate thermal engagement between the heating assembly and the humidification chamber when the humidification chamber is in the operating position.

7. The apparatus according to claim 1, wherein the heating assembly is arranged to face outwardly from an external wall of the main body.

8. The apparatus according to claim 1, wherein the heating assembly is arranged on the platform and the heating assembly and the humidification chamber engage when the humidification chamber is in the operating position.

9. The apparatus according to claim 8, wherein the heating assembly is arranged on an inner portion of the platform and the humidification chamber is configured to be seated on the heating assembly which engages the heating assembly and the humidification chamber.

10. The apparatus according to claim 9, wherein pivoting the platform can be pivoted into the closed orientation in which the act of closing the platform moves an auxiliary flow path to an active position, and pivoting the platform can be pivoted into the opened orientation in which the act of opening the platform moves the auxiliary flow path to an inactive position.

11. The apparatus according to claim 10, wherein when the platform is in the opened orientation, the humidification chamber may be loaded onto the platform, and the heating assembly engages the humidification chamber for heating water in the humidification chamber.

12. The apparatus according to claim 1, wherein the apparatus comprises an auxiliary flow path that is operably connected to the housing so as to move between:

i) an active position in which the auxiliary flow path communicates with the housing outlet port and the housing inlet port to convey the gas stream therebetween when the apparatus is in the non-humidification mode, and ii) an inactive position in which the auxiliary flow path is remote from the housing outlet port and the housing inlet port so the humidification chamber is configured to be located in the operating position when the apparatus is in the humidifying mode.

13. The apparatus according to claim 12, wherein the auxiliary flow path is arranged on the platform and is in the active position when the platform is closed against the main body, and is in the inactive position when the platform is pivoted away from the main body.

* * * * *